(12) United States Patent
Kato et al.

(10) Patent No.: US 6,823,045 B2
(45) Date of Patent: Nov. 23, 2004

(54) MULTI-LEAF COLLIMATOR AND MEDICAL SYSTEM INCLUDING ACCELERATOR

(75) Inventors: Kohei Kato, Hitachi (JP); Hiroshi Akiyama, Hitachiohta (JP); Masaki Yanagisawa, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/676,059

(22) Filed: Oct. 2, 2003

(65) Prior Publication Data

US 2004/0062353 A1 Apr. 1, 2004

Related U.S. Application Data

(63) Continuation of application No. 09/943,385, filed on Aug. 31, 2001.

(30) Foreign Application Priority Data

Jan. 30, 2001 (JP) ........................................ 2001-021964

(51) Int. Cl.[7] ................................................ G21K 1/04
(52) U.S. Cl. ...................................................... 378/152
(58) Field of Search ................................. 378/145, 147, 378/148, 149, 150, 151, 152, 153; 250/505.1

(56) References Cited

U.S. PATENT DOCUMENTS

| | | | | |
|---|---|---|---|---|
| 4,754,147 A | * | 6/1988 | Maughan et al. | 250/505.1 |
| 4,794,629 A | * | 12/1988 | Pastyr et al. | 378/152 |
| 4,868,844 A | * | 9/1989 | Nunan | 378/152 |

* cited by examiner

Primary Examiner—Edward J. Glick
Assistant Examiner—Courtney Thomas
(74) Attorney, Agent, or Firm—Crowell & Moring LLP

(57) ABSTRACT

The invention is intended to shorten a positioning time required for forming an irradiation area with high accuracy using a number of leaf plates, and to reduce physical and mental burdens imposed on patients. A multi-leaf collimator comprises leaf plate driving body each including a plurality of movable leaf plates and provided respectively on one side and the other side, the plurality of leaf plates of the leaf plate driver on one side and the plurality of leaf plates of the leaf plate driver on the other side being disposed in an opposing relation to form an irradiation field of a radiation beam between the opposing leaf plates. Each of the leaf plate driving body includes a motor provided in common to the plurality of leaf plates. Driving force of the motor can be transmitted to the plurality of leaf plates at the same time through a pinion gear, upper and lower air cylinders, and upper and lower guides. Also, the driving force can be cut off selectively for each leaf plate.

15 Claims, 12 Drawing Sheets

MULTI-LEAF COLLIMATOR AND MEDICAL SYSTEM INCLUDING ACCELERATOR

This application is a continuation of application Ser. No. 09/943,385, filed Aug. 31, 2001.

BACKGROUND AND SUMMARY OF THE INVENTION

1. Field of the Invention

The present invention relates to a multi-leaf collimator for, when a radiation beam is irradiated to a target inside a radiation object, forming an irradiation area of the radiation beam in match with a target shape. The present invention also relates to a medical system including an accelerator.

2. Description of the Related Art

In one typical example for irradiating a radiation beam (e.g., a charged particle beam) to a target inside a radiation object, the radiation beam is irradiated to cancer cells (referred to as "diseased part" hereinafter) in a patient body. In such a case, the radiation object corresponds to the patient, and the target corresponds to the diseased part.

When irradiating a radiation beam to the diseased part in a patient body, if an irradiation area of the radiation beam does not match with a target shape, the radiation beam is also irradiated to a normal part around the diseased part. Irradiation of the radiation beam, which has been emitted for remedy of the diseased part, to the normal part around the diseased part may adversely affect the normal part. It is therefore important to define the irradiation area precisely in match with the diseased part, and to minimize irradiation of the radiation beam to the normal part.

A multi-leaf collimator is known as one solution for forming an irradiation area in match with a shape of the diseased part to avoid a radiation beam from being irradiated to the normal part that should be protected against the irradiation.

Such a multi-leaf collimator comprises two leaf plate driving body each including a number of movable shield plates (leaf plates), which are capable of shielding the radiation beam and disposed in the multi-layered form. The leaf plates are arranged so as to sandwich a propagation path of a radiation beam emitted from a radiation source toward the diseased part, and ends of the leaf plates of the two leaf plate driving body are positioned to face each other so that an irradiation field of the radiation beam is formed between the opposing ends. In each leaf plate driver, positions of the leaf plates are individually adjusted by the driving force of driving means, such as an electric motor, to form a space gap, which is similar to the irradiation area, between the leaf plates of one leaf plate driver and the leaf plates of the other leaf plate driver, thereby allowing passage of only the radiation beam that propagates toward the desired irradiation area. Then, the radiation beam having passed the space gap forms the irradiation field, shaped as desired, at the position of the diseased part. With the construction described above, of the radiation beam having reached the multi-leaf collimator, a component directing to other areas than the irradiation area is shielded by the leaf plates, and therefore the irradiation to an unnecessary part (normal part other than the diseased one) can be prevented.

To improve the accuracy in forming contours of the irradiation field when the multi-leaf collimator is used to define the desired shape of the irradiation field, it is required not only to employ a number of leaf plates having a smaller thickness, but also to position each leaf plate with high accuracy. U.S. Pat. No. 4,794,629, for example, is known as the related art in consideration of that point. In a multi-leaf collimator according to that related art, a leaf plate driver on one side and a leaf plate driver on the other side each comprise a number of leaf plates having gears provided at upper edges thereof, a single unit of driving means provided in common to all the leaf plates for adjusting positions of the leaf plates, and a gearing mechanism brought into mesh with the gears of the leaf plates for transmitting the driving force from the driving means. The gearing mechanism is slid in the thickness direction of the leaf plate to be meshed with the gear of each leaf plate successively so that the driving force from the driving means is transmitted to the leaf plates one by one. Each leaf plate can be thereby positioned at a desired position.

The above-cited related art, however, has the problem as follows.

The related art is constructed, as described above, such that the gearing mechanism is brought into mesh with the gear of each leaf plate successively for driving each leaf plate to the desired position in sequence. When forming the irradiation area in practice, therefore, a number of leaf plates must be positioned successively one by one, and a time taken to complete the formation of the irradiation area is prolonged. This results in difficulties in shortening a remedy time, and hence in reducing physical and mental burdens imposed on patients.

SUMMARY OF THE INVENTION

Accordingly, it is an object of the present invention to provide a multi-leaf collimator and a medical system including an accelerator, which can shorten a positioning time required for forming an irradiation field with high accuracy by using a number of leaf plates, and can reduce physical and mental burdens imposed on patients.

(1) To achieve the above object, the present invention provides a multi-leaf collimator comprising leaf plate driving body each including a plurality of movable leaf plates and provided respectively on one side and the other side, the plurality of leaf plates of the leaf plate driver on one side and the plurality of leaf plates of the leaf plate driver on the other side being disposed in an opposing relation to form an irradiation field of a radiation beam between the opposing leaf plates, wherein each of the leaf plate driving body comprises one driving unit provided in common to the plurality of leaf plates; and driving force transmitting/cutoff mechanisms capable of transmitting driving force of the one driving unit to the plurality of leaf plates at the same time and cutting off the driving force selectively for each leaf plate.

With the present invention, in each of the leaf plate driving body, the driving force transmitting/cutoff mechanisms enable the driving force of one common driving unit to be transmitted to a plurality of leaf plates at the same time, and also enable the driving force to be selectively cut off for each leaf plate. For example, when driving each leaf plate from the origin position to the set position, the driving force is transmitted to the plurality of leaf plates at the same time through the driving force transmitting/-cutoff mechanisms, causing all the leaf plates to start movement simultaneously. Then, when one leaf plate reaches the set position, the driving force applied to the relevant leaf plate is cut off to leave it at the set position. By repeating such a step, all the leaf plates can be successively positioned to the set positions. Conversely, when returning all the leaf plates to the origin positions from the set condition, the driving force is transmitted to the leaf plates in the different set positions at the same time through the driving force transmitting/cutoff mechanisms, causing all the leaf plates to start movement simultaneously while they remain in the transversely not-aligned state. Then, when one leaf plate returns to the origin position, the driving force applied to the relevant leaf plate is cut off to hold it at the origin position. By repeating such a step, all the leaf plates can be successively returned to the origin positions.

Thus, the present invention enables the leaf plates to be successively positioned in each of the leaf plate driving body while moving a plurality of leaf plates at the same time. Therefore, when the irradiation field is formed with high accuracy, a time required for completing the formation of the irradiation field can be shortened in comparison with a conventional structure wherein a number of leaf plates must be positioned one by one successively in each leaf plate driver. As a result, physical and mental burdens imposed on patients can be reduced.

(2) To achieve the above object, the present invention also provides a multi-leaf collimator comprising leaf plate driving body each including a plurality of movable leaf plates and provided respectively on one side and the other side, the plurality of leaf plates of the leaf plate driver on one side and the plurality of leaf plates of the leaf plate driver on the other side being disposed in an opposing relation to form an irradiation field of a radiation beam between the opposing leaf plates, wherein each of the leaf plate driving body comprises one driving force generating mechanism provided to be capable of transmitting driving force to the plurality of leaf plates at the same time; and a plurality of engaging/disengaging mechanisms provided in a one-to-one relation to the plurality of leaf plates and being each capable of selectively engaging and disengaging a corresponding leaf plate with and from the one driving force generating mechanism.

(3) In the above (1) or (2), preferably, each of the leaf plate driving body further comprises one or more holding members capable of abutting against the leaf plates to hold the leaf plates in stationary positions.

(4) To achieve the above object, a medical system including an accelerator, according to the present invention, comprises an accelerator; and an irradiator having a collimator through which a radiation beam emitted from the accelerator passes, and irradiating the beam having passed the collimator, the collimator comprising leaf plate driving body each including a plurality of movable leaf plates and provided respectively on one side and the other side, the plurality of leaf plates of the leaf plate driving body being disposed in an opposing relation to form an irradiation field of the radiation beam between the opposing leaf plates, each of the leaf plate driving body comprising one driving unit provided in common to the plurality of leaf plates, and driving force transmitting/cutoff mechanisms capable of transmitting driving force of the one driving unit to the plurality of leaf plates at the same time and cutting off the driving force selectively for each leaf plate.

(5) To achieve the above object, a medical system including an accelerator, according to the present invention, comprises an accelerator; and an irradiator having a collimator through which a radiation beam emitted from the accelerator passes, and irradiating the beam having passed the collimator, the collimator comprising leaf plate driving body each including a plurality of movable leaf plates and provided respectively on one side and the other side, the plurality of leaf plates of the leaf plate driving body being disposed in an opposing relation to form an irradiation field of the radiation beam between the opposing leaf plates, each of the leaf plate driving body comprising one driving force generating mechanism provided to be capable of transmitting driving force to the plurality of leaf plates at the same time, and a plurality of engaging/disengaging mechanisms provided in a one-to-one relation to the plurality of leaf plates and being each capable of selectively engaging and disengaging a corresponding leaf plate with and from the one driving force generating mechanism.

(6) To achieve the above object, a medical system including an accelerator, according to the present invention, comprises an accelerator; and a rotating irradiator including an irradiator having a collimator through which a radiation beam emitted from the accelerator passes, and irradiating the beam having passed the collimator, the collimator comprising leaf plate driving body each including a plurality of movable leaf plates and provided respectively on one side and the other side, the plurality of leaf plates of the leaf plate driving body being disposed in an opposing relation to form an irradiation field of the radiation beam between the opposing leaf plates, each of the leaf plate driving body comprising one driving unit provided in common to the plurality of leaf plates, and driving force transmitting/cutoff mechanisms capable of transmitting driving force of the one driving unit to the plurality of leaf plates at the same time and cutting off the driving force selectively for each leaf plate.

(7) To achieve the above object, a medical system including an accelerator, according to the present invention, comprises an accelerator; and a rotating irradiator including an irradiator having a collimator through which a radiation beam emitted from the accelerator passes, and irradiating the beam having passed the collimator, the collimator comprising leaf plate driving body each including a plurality of movable leaf plates and provided respectively on one side and the other side, the plurality of leaf plates of the leaf plate driving body being disposed in an opposing relation to form an irradiation field of the radiation beam between the opposing leaf plates, each of the leaf plate driving body comprising one driving force generating mechanism provided to be capable of transmitting driving force to the plurality of leaf plates at the same time, and a plurality of engaging/disengaging mechanisms provided in a one-to-one relation to the plurality of leaf plates and being each capable of selectively engaging and disengaging a corresponding leaf plate with and from the one driving force generating mechanism.

(8) In the above (4) or (6), preferably, the medical system further comprises a control unit for controlling the one driving unit and the driving force transmitting/cutoff mechanisms.

(9) In the above (5) or (7), preferably, the medical system further comprises a control unit for controlling the one driving force generating mechanism and the engaging/disengaging mechanisms.

DESCRIPTION OF THE PREFERRED EMBODIMENTS

Embodiments of the present invention will be described below in detail with reference to the drawings.

A first embodiment of the present invention will be described with reference to FIGS. 1 to 9.

Figure 2:
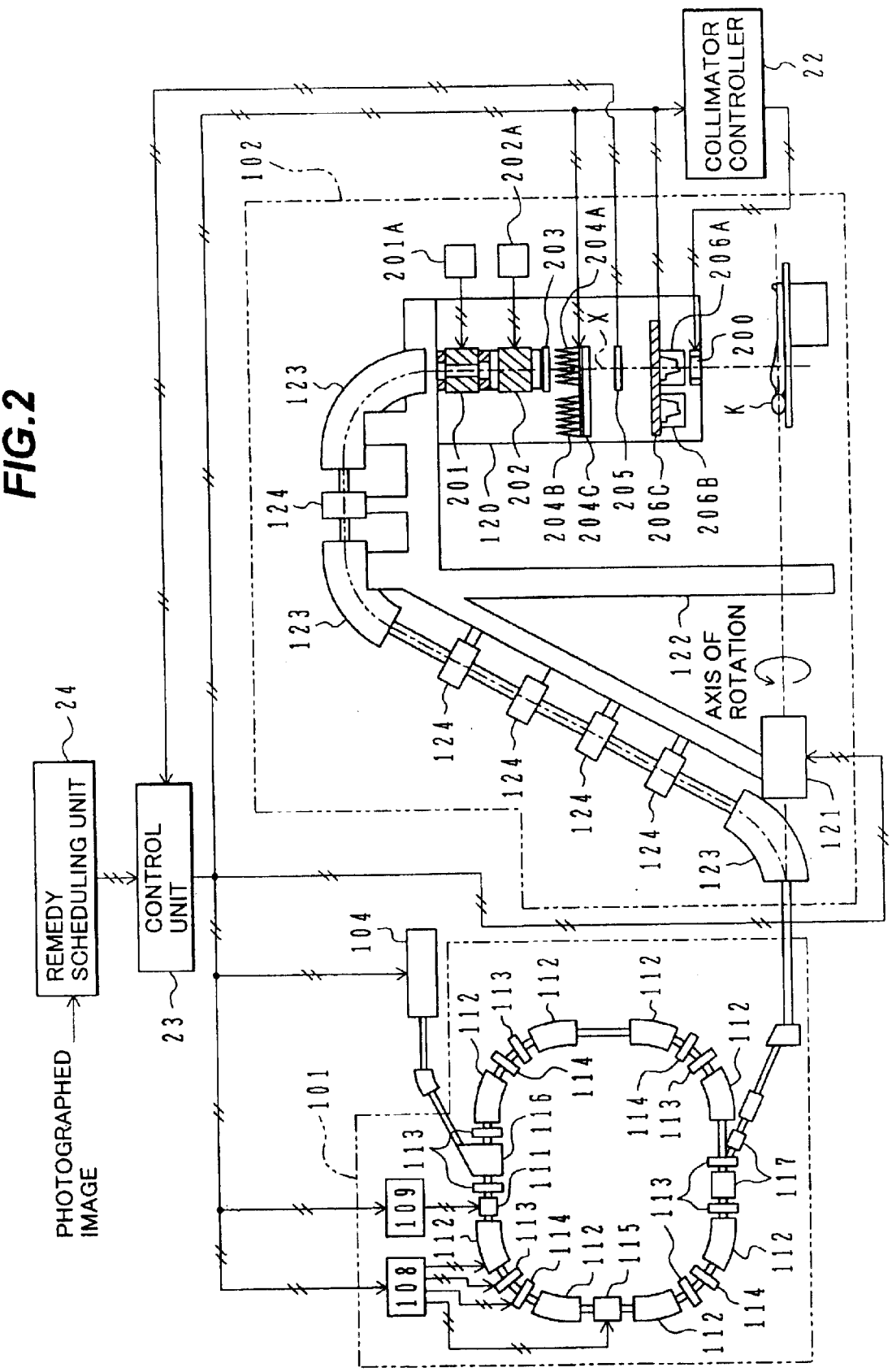
FIG. 2 is a conceptual block diagram showing an overall system configuration of a medical system including a radiation beam irradiator comprising the multi-leaf collimator shown FIG. 1 and an accelerator.

FIG. 2 is a conceptual block diagram showing an overall system configuration of a medical system including a radiation beam irradiator comprising a multi-leaf collimator of this embodiment and an accelerator.

In the radiation beam irradiator, a radiation beam (also referred to simply as a "beam" hereinafter), such as a charged particle beam, accelerated by an accelerator (synchrotron) 101 is outputted from a rotating irradiator 102 under control of a control unit 23 for irradiation to the diseased part of a patient K. By turning the rotating irradiator 102 about an axis of the rotation, the beam can be irradiated to the diseased part from a plurality of directions.

(1) Outline and Operation of Synchrotron 101

The synchrotron 101 comprises a high-frequency applying apparatus 111 for applying a high-frequency magnetic field and electric field (referred to together as a "high-frequency electromagnetic field" hereinafter) to the beam to increase the amplitude of betatron oscillation of the beam; deflecting electromagnets 112 for bending a track of the beam; quadrupole electromagnets 113 for controlling the betatron oscillation of the beam; hexapole electromagnets 114 for exciting resonance for exiting of the beam; a high-frequency accelerating cavity 115 for accelerating the beam; an inlet unit 116 for introducing the beam into the synchrotron 101, and outlet deflectors 117 for guiding the beam to exit the synchrotron 101.

When the control unit 23 outputs an emission command to a pre-stage accelerator 104, the pre-stage accelerator 104 emits a beam of low energy in accordance with the emission command. The beam is guided to the inlet unit 116 of the synchrotron 101 through a beam transporting system, and then introduced to the synchrotron 101. The introduced beam goes around within the synchrotron 101 while its track is bent by the deflecting electromagnets 112. While the beam is going around within the synchrotron 101, it undergoes the betatron oscillation under actions of the quadrupole electromagnets 113. The oscillation frequency of the betatron oscillation is properly controlled in accordance with the amount of excitation of the quadrupole electromagnets 113 so that the beam stably orbits within the synchrotron 101. During the orbiting, a high-frequency magnetic field is applied to the beam in the high-frequency accelerating cavity 115, whereby energy is applied to the beam. As a result, the beam is accelerated and the beam energy is increased.

When the energy of the beam orbiting within the synchrotron 101 is increased to a level of energy E, the application of energy to the beam in the high-frequency accelerating cavity 115 is stopped. At the same time, a gradient of the beam orbit is changed under well-known control by the quadrupole electromagnets 113, the hexapole electromagnets 114 and the high-frequency applying apparatus 111. The magnitude of the betatron oscillation is hence abruptly increased due to resonance, causing the beam to exit the synchrotron 101 through the outlet deflectors 117.

In the above-described operation of the synchrotron 101, in accordance with the depth position of the diseased part inputted from a remedy scheduling unit 24 (described later in detail), the control unit 23 determines the energy E of the beam that is to be irradiated to the diseased part in a predetermined irradiating direction (usually the beam is irradiated in plural directions). Further, the control unit 23 calculates patterns of current values supplied to the deflecting electromagnets 112, the quadrupole electromagnets 113 and the high-frequency accelerating cavity 115 for accelerating the beam in the synchrotron 101 to a level of the energy E, and also calculates current values supplied to the high-frequency applying apparatus 111 and the hexapole electromagnets 114 for emitting the beam of the energy E. The calculated current values are stored in a storage means in the control unit 23 corresponding to levels of the energy E for each component, and are outputted to a power supply 108 or 109 when the beam is accelerated or exits.

(2) Outline and Operation of Rotating Irradiator 102

The beam exiting the synchrotron 101 enters the rotating irradiator 102. The rotating irradiator 102 comprises a gantry 122, on which deflecting electromagnets 123, quadrupole electromagnets 124 and an outlet nozzle 120 are mounted, and a motor 121 for rotating the gantry 122 about a predetermined axis of rotation (see FIG. 2).

The beam having entered the rotating irradiator 102 is introduced to the outlet nozzle 120 while the beam track is bent by the deflecting electromagnets 123 and the betatron oscillation is adjusted by the quadrupole electromagnets 124. The beam introduced to the outlet nozzle 120 first passes between scanning electromagnets 201, 202. Sinusoidal AC currents being 90 degrees out of phase are supplied to the scanning electromagnets 201, 202 from power supplies 201A, 202A. The beam passing between magnet poles of the scanning electromagnets 201, 202 is deflected by magnetic fields generated from the scanning electromagnets 201, 202 so that the beam makes a circular scan at a position of the diseased part.

The beam having passed the scanning electromagnets 201, 202 is diffused by a diffuser 203 so as to have an enlarged diameter, and then passes a ridge filter 204A (or 204B). The ridge filter 204A (or 204B) attenuates the beam energy at such a predetermined rate that the beam energy has a distribution corresponding to a thickness of the diseased part. The radiation dose is then measured by a dosimeter 205. Thereafter, the beam is introduced to a porous member 206A (or 206B) that gives the beam an energy distribution corresponding to a bottom shape of the diseased part. Further, the beam is shaped by a multi-leaf collimator 200 in match with a horizontal shape of the diseased part, and then irradiated to the diseased part.

Usually, as mentioned above, the beam is irradiated to the diseased part from a plurality of directions. This embodiment shows, by way of example, the case of irradiating the diseased part from two directions. Two ridge filters 204A, 204B are fabricated beforehand for each of the two irradiating directions corresponding to respective values of thickness of the diseased part determined by the remedy scheduling unit 24. Also, the porous members 206A, 206B are fabricated beforehand for each of the two irradiating directions corresponding to respective bottom shapes of the diseased part determined by the remedy scheduling unit 24. The fabricated ridge filters 204A, 204B are mounted on a rotating table 204C, and the fabricated porous members 206A, 206B are mounted on a rotating table 206C. An axis of rotation of the rotating table 206C is offset from the center of the beam track. By turning the rotating table 206C, therefore, the porous member 206A or 206B can be alternately arranged to lie across the beam track, and the beam having an energy distribution corresponding to each of the two irradiating directions can be formed. Additionally, the rotating table 206C is of the same construction as the rotating table 204C.

When setting or changing the irradiating direction, an inclination angle signal corresponding to the irradiating direction is outputted from the control unit 23 to the motor 121, whereupon the motor 121 rotates the gantry 122 to an inclination angle indicated by the outputted signal and the rotating irradiator 102 is moved to a position where it is able to irradiate the beam to the diseased part from the selected irradiating direction. Also, the control unit 23 outputs, to the rotating tables 204C and 206C, signals for instructing them to arrange the ridge filter 204A (or 204B) and the porous member 206A (or 206B), corresponding to the selected irradiating direction, so as to lie across the beam track. The rotating tables 204C, 206C are rotated in accordance with the instruction signals.

Figure 3:
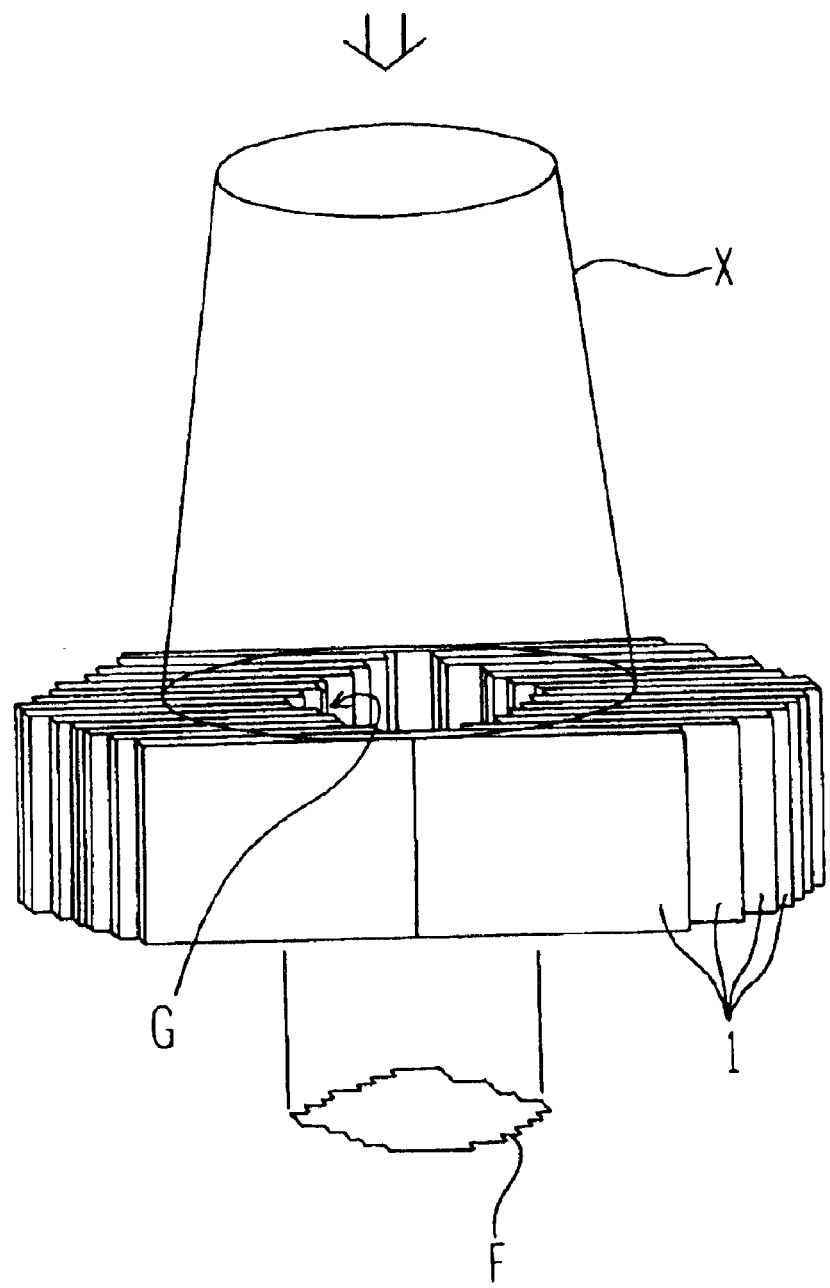
FIG. 3 is a view showing a manner of forming an irradiation area of the radiation beam by the multi-leaf collimator shown in FIG. 1.

Then, a control signal corresponding to the selected irradiating direction is outputted from the control unit 23 to a collimator controller (leaf position control computer) 22. Responsively, the collimator controller 22 makes control such that, as shown in FIG. 3, a number of leaf plates 1 (described later in detail) provided in the multi-leaf collimator 200 are positioned in an opposing relation to provide a gap space G, which defines an irradiation area (field) F of a beam X in match with a horizontal shape of the diseased part as viewed in the selected irradiating direction. As a result, of the beam having reached the multi-leaf collimator 200 after passing the porous member 206A (or 206B), a component directing to other areas than the irradiation field F is shielded by the leaf plates, and the irradiation to an unnecessary part can be prevented.

Important features of the present invention reside in mechanisms for driving the leaf plates of the multi-leaf collimator 200. Details of those features will be described below in sequence.

(3) Basic Construction and Operation of Multi-leaf Collimator 200

Figure 1:
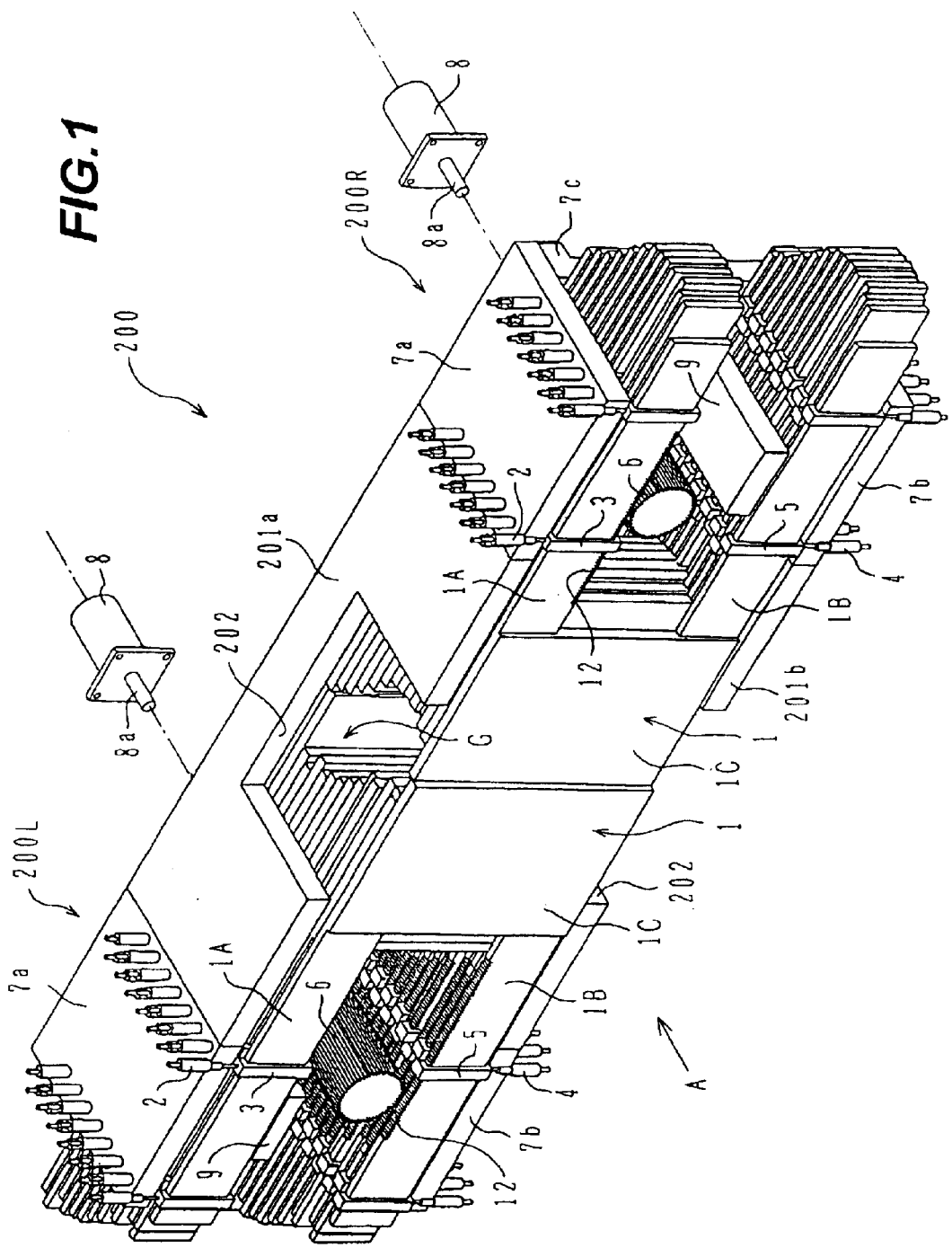
FIG. 1 is a perspective view showing the detailed structure of a multi-leaf collimator according to a first embodiment of the present invention.
Figure 4:
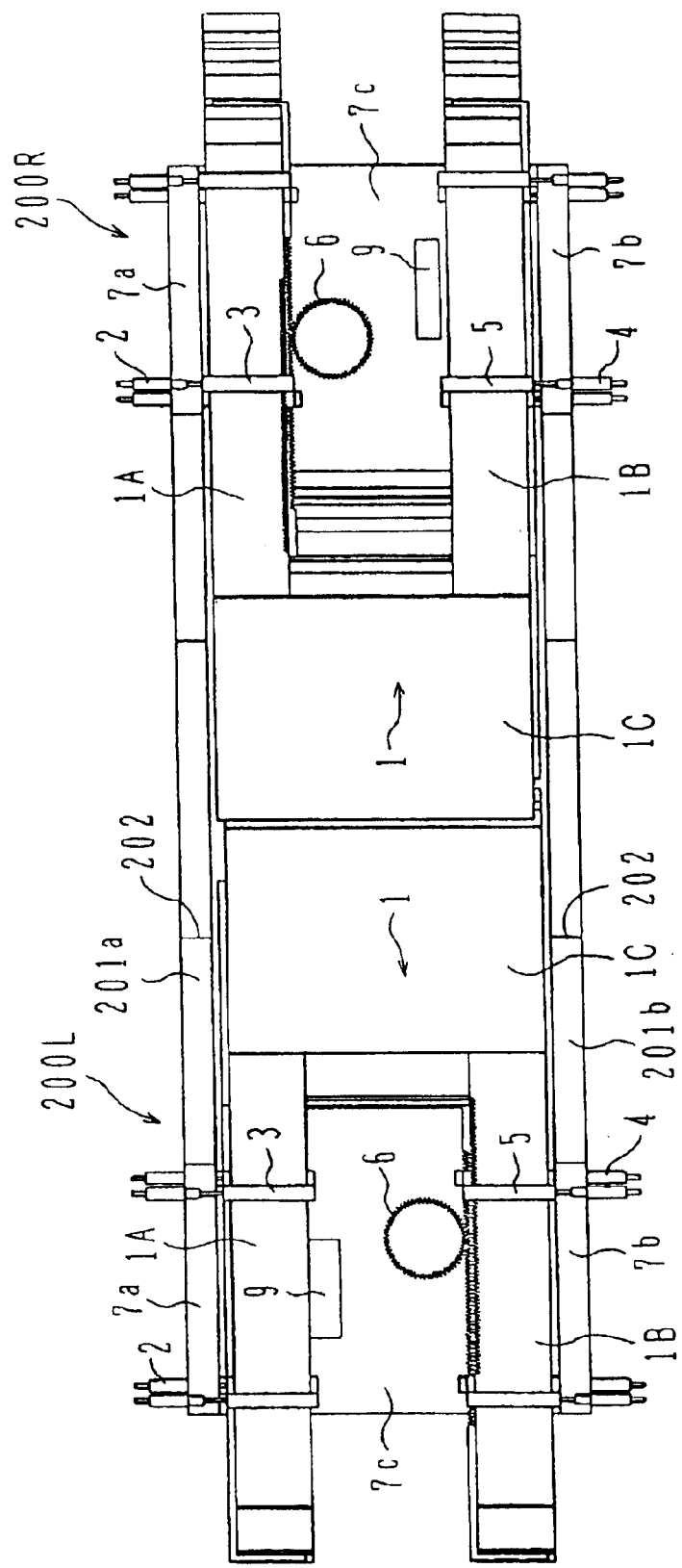
FIG. 4 is a front view of the multi-leaf collimator as viewed in the direction of A in FIG. 1.
Figure 5:
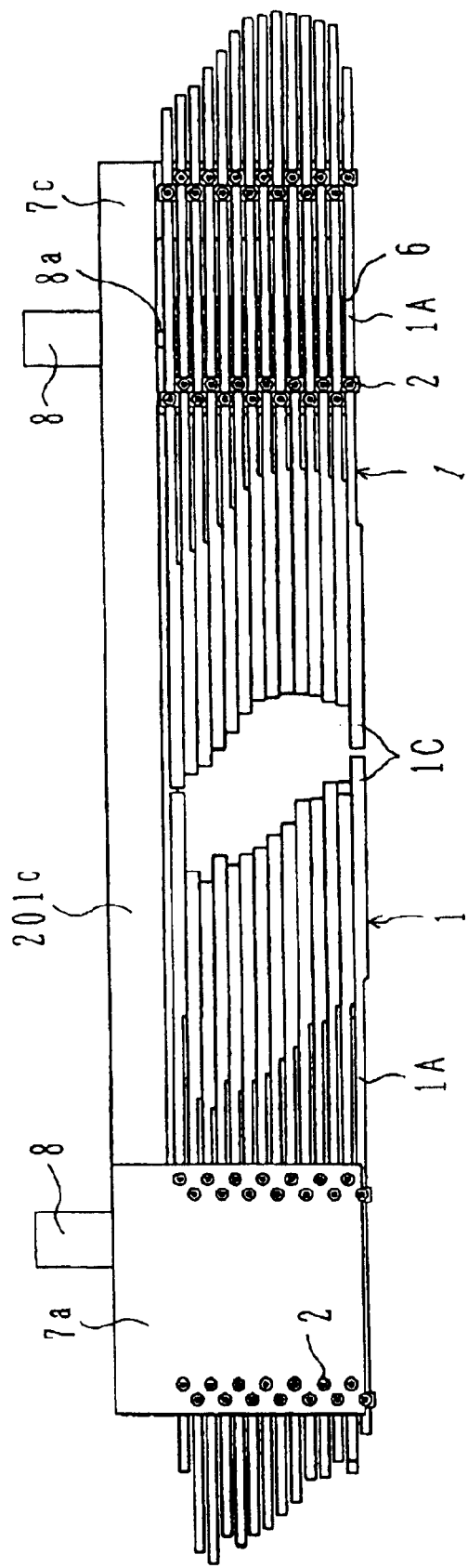
FIG. 5 is a plan view of the multi-leaf collimator in a state where an upper coupling portion and an upper support of a leaf plate driver are removed from FIG. 1.
Figure 6:
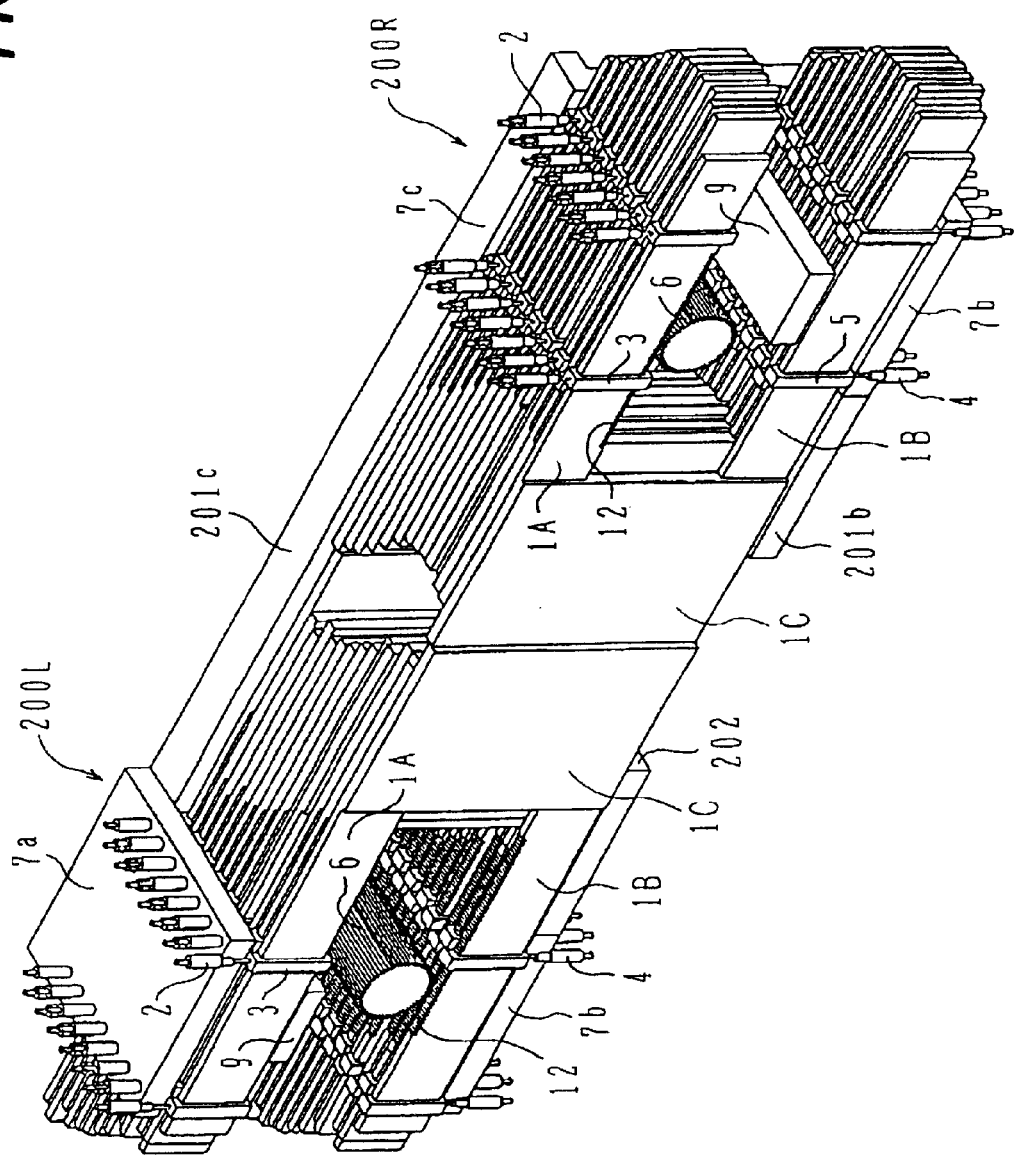
FIG. 6 is a plan view of the multi-leaf collimator as viewed in the direction of B in FIG. 5.

FIG. 1 is a perspective view showing the detailed structure of the multi-leaf collimator 200; FIG. 4 is a front view as viewed in the direction of A in FIG. 1; FIG. 5 is a plan view of the multi-leaf collimator in a state where an upper coupling portion 201a (described later) and an upper support 7a (described later) of a leaf plate driver 200R (described later); and FIG. 6 is a plan view as viewed in the direction of B in FIG. 5.

Referring to FIGS. 1, 4, 5 and 6, the multi-leaf collimator 200 comprises leaf plate driving body 200L and 200R.

Each leaf plate driver 200L or 200R comprises a plurality (twelve in this embodiment, but the number may be greater than it) of leaf plates 1, which are movable to form the irradiation field F of the radiation beam and capable of shielding the radiation beam; an upper guide 3 and a lower guide 5 for receiving an upper sliding portion 1A and a lower sliding portion 1B of each leaf plate 1, respectively, and supporting them to be slidable in the longitudinal direction of the leaf plate 1 (left and right direction in FIG. 4); upper air cylinders 2 and lower air cylinders 4 capable of pressing the upper guide 3 and the lower guide 5 upward and downward, respectively; a support structure 7 including an upper support 7a and a lower support 7b for fixedly supporting the upper air cylinders 2 and the lower air cylinders 4, respectively, and an intermediate portion 7c connecting the upper support 7a and the lower support 7b; a motor 8 provided as a driving source for the leaf plates 1; a pinion gear 6 disposed coaxially with a drive shaft 8a of the motor 8 and connected to the drive shaft 8a on the side of the intermediate portion 7c; and a braking plate 9 brought into contact with the leaf plates 1 for holding them stationary by frictional forces (as described later in detail).

The motor 8 is a known servo motor in this embodiment. A motor and a rotary encoder are coaxially arranged as an integral unit, and a pulse signal is outputted for each certain small angle of rotation.

The upper air cylinders 2 and the lower air cylinders 4 are each constituted by a known single- or double-actuated air cylinder. For example, a piston is disposed in a cylindrical cylinder chamber, and a rod projecting out of the cylinder chamber is attached to the piston. In an operative condition, compressed air from a compressed air source is supplied to a bottom-side chamber, whereupon the piston is moved to the rod side by overcoming the biasing force of a spring disposed on the rod side. As a result, the rod is extended. Upon shift to an inoperative (stop) condition, the compressed air supplied to the bottom-side chamber is discharged (for example, by being made open to the atmosphere), whereby the piston is returned to the bottom side by the biasing force of the spring. As a result, the rod is contracted for return to the original position.

The leaf plate 1 comprises upper and lower sliding portions 1A, 1B inserted in the upper and lower guides 3, 5, respectively, and a shield portion 1C coupling the upper and lower sliding portions 1A, 1B and shielding the radiation beam. The shield portions 1C of every two adjacent leaf plates 1 are arranged to be able to slide in a close contact relation. To that end, the upper and lower sliding portions 1A, 1B are each formed to have a smaller thickness than the shield portion 1C for securing spaces necessary for installing the upper and lower guides 3, 5. Also, to that end, the upper and lower guides 3, 5 and the upper and lower air cylinders 2, 4 associated with the adjacent leaf plates 1 are arranged in an alternately displaced relation (in a zigzag pattern), as shown in FIGS. 1, 5 and 6.

A rack gear 12 is partly provided on an upper edge of the lower sliding portion 1B of each leaf plate 1 in the leaf plate driver 200L. The aforesaid pinion gear 6 is arranged in a position where it is able to engage (mesh) with the rack gear 12. On the other hand, the aforesaid braking plate 9 is disposed opposite to a lower edge of the upper sliding portion 1A of each leaf plate 1 in the leaf plate driver 200L.

When moving the leaf plate 1, the lower air cylinder 4 is set to the operative condition and the upper air cylinder 2 is set to the inoperative (stop) condition, whereupon the leaf plate 1 is moved upward to mesh the rack gear 12 with the pinion gear 6, while the lower edge of the upper sliding portion 1A is moved away (disengaged) from an upper surface of the braking plate 9. By operating the motor 8 in such a state, the leaf plate 1 can slide in the predetermined direction through transmission of the driving force of the motor 8. Then, when stropping the leaf plate 1, the motor 8 is first stopped to cease the movement of the leaf plate 1. After that, by setting the upper air cylinder 2 to the operative condition and the lower air cylinder 4 to the inoperative condition, the leaf plate 1 is moved downward to release the rack gear 12 from mesh with the pinion gear 6, while the lower edge of the upper sliding portion 1A is partly brought into abutment against the upper surface of the braking plate 9. The leaf plate 1 is thereby positively held stationary at that position.

Likewise, in the leaf plate driver 200R, a rack gear 12 is partly provided on a lower edge of the upper sliding portion 1A of each leaf plate 1, and the aforesaid braking plate 9 is disposed opposite to an upper edge of the lower sliding portion 1B. By setting the upper air cylinder 2 to the operative condition, the leaf plate 1 is moved downward to mesh the rack gear 12 with the pinion gear 6 so that the leaf plate 1 slides by the driving force of the motor 8, while the upper edge of the lower sliding portion 1B is moved away from a lower surface of the braking plate 9. Also, by setting the lower air cylinder 4 to the operative condition, the leaf plate 1 is moved upward to release the rack gear 12 from mesh with the pinion gear 6, while the upper edge of the lower sliding portion 1B is partly brought into abutment against the lower surface of the braking plate 9. The leaf plate 1 is thereby positively held stationary at that position.

An upper coupling portion 201a, a lower coupling portion 201b, and an intermediate coupling portion 201c (see FIGS. 5 and 6) are disposed respectively between the upper supports 7a, between the lower supports 7b, and between the intermediate supports 7c of the leaf plate driving body 200L, 200R for coupling them. Of those coupling portions, the upper and lower coupling portions 201a, 201b have cutouts 202 formed therein to allow passage of the radiation beam.

(4) Control System (4-1) Overall Construction

Figure 7:
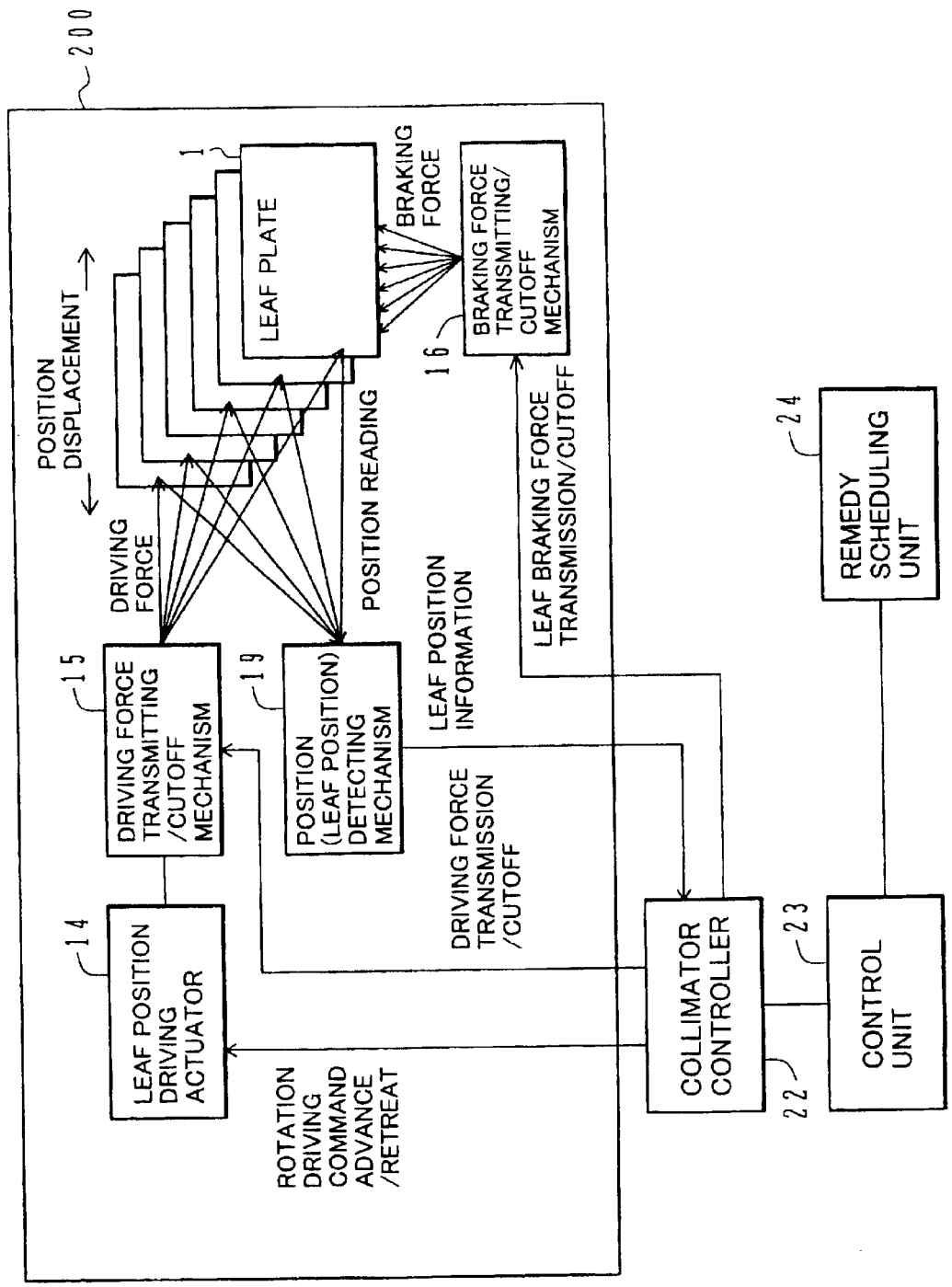
FIG. 7 is a functional block diagram showing a system configuration of a control system in a medical system including the multi-leaf collimator shown in FIG. 1.

FIG. 7 is a functional block diagram showing a system configuration of a control system in a medical system including the multi-leaf collimator 200 of this embodiment. In addition to the remedy scheduling unit 24, the control unit 23 and the collimator controller 22 mentioned above, the control system further comprises a leaf position driving actuator 14 (servo motor 8 in this embodiment) controlled in accordance with a rotation driving command and a driving stop command from the collimator controller 22; a driving force transmitting/cutoff mechanism 15 (upper and lower air cylinders in this embodiment) controlled in accordance with a driving force transmitting command and a driving force cutoff command from the collimator controller 22; a braking force transmitting/cutoff mechanism 16 (upper and lower air cylinders in this embodiment, described later in detail) controlled in accordance with a braking force transmitting command and a braking force cutoff command from the collimator controller 22; and a position detecting mechanism 19 (servo motor 8 in this embodiment, described later in detail) for outputting a position detected signal for each leaf plate 1 to the collimator controller 22.

It is to be noted that, as described above, this embodiment is arranged to transmit or cut off the driving force from the pinion gear 6 and to cut off or transmit the braking force from the braking plate 9 at the same time, and switching between transmission and cut off of the driving force or the braking force is performed by the upper and lower air cylinders cylinders 2, 4. Consequently, the driving force transmitting/cutoff mechanism 15 and the braking force transmitting/cutoff mechanism 16 are constituted by a common mechanism. Further, the driving force transmitting command serves also as the braking force cutoff command, and the driving force cutoff command serves also as the braking force transmitting command.

(4-2) Remedy Scheduling Unit 24

The remedy scheduling unit 24 comprises, for example, a computer, a plurality of display devices, an input device, and a patient database (the patient database may be separately prepared and connected to the unit 24 via a network). The remedy scheduling unit 24 has the function of aiding the remedy scheduling work to be made by a doctor as a pre-stage for carrying out actual irradiation. Practical examples of the remedy scheduling work include identification of the diseased part, decision of the irradiation area and the irradiating directions, decision of the radiation dose irradiated to the patient, and calculation of a dose distribution in the patient body.

(A) Identification of Diseased Part

In a diagnosis prior to the remedy, for example, three-dimensional image data of a tumor in the patient body is taken beforehand by an X-ray CT inspection and an MRI inspection. Those inspection data is given with a number for each patient, and is stored and managed as digital data in the patient database. In addition to the inspection data, the patient database also contains information such as the name of patient, the patient number, the age, height and weight of patient, the diagnosis and inspection records, historical data for diseases that the patient has suffered, historical data for remedies that the patient has taken, and remedy data. Stated otherwise, all data necessary for remedy of the patient is recorded and managed in the patient database. The doctor can access the patient database, as required, to acquire the image data of the diseased part and display the image data on the display devices of the remedy scheduling unit 24. Specifically, it is possible to display the image data of the diseased part as a three-dimensional image looking from any desired direction, and as a sectional image sliced at each of different depths looking from any desired direction. Further, the remedy scheduling unit 24 has the functions of assisting the doctor to identify the diseased part, such as contrast highlighting and area painting-out with a certain gradation level as a threshold for each image. The doctor identifies an area of the diseased part by utilizing those assistant functions.

(B) Tentative Selection of Irradiation Area and Irradiating Directions

Subsequently, the doctor makes an operation to decide the irradiation area that envelops the diseased part and includes an appropriate margin in consideration of a possibility that the diseased part may move in the patient body due to breathing, for example. Further, the doctor selects several irradiating directions out of interference with the internal organs highly susceptible to radiation, such as the spine.

(C) Decision of Contour of Irradiation Field

Based on the several irradiating directions, an image of the irradiation field looking from each irradiating direction is displayed, and the contour of the irradiation field covering the whole of a tumor is displayed in a highlighted manner. Also, a three-dimensional image of the diseased part is displayed, and a position of a maximum section and a three-dimensional shape subsequent to the maximum section are displayed. Those images are displayed on a plurality of display screens separately, or on one display screen in a divided fashion. Herein, the contour of the irradiation field decided provides basic (original) data for the irradiation field F shaped by the multi-leaf collimator 200, and the three-dimensional shape data subsequent to the maximum section provides basic (original) data for irradiation compensators, such as the porous members 206A, 206B.

(D) Decision of Irradiating Direction and Radiation Dose Irradiated to Patient

The remedy scheduling unit 24 has the function of automatically deciding a position of each leaf plate 1 of the multi-leaf collimator 200 based on information regarding the contour of the irradiation field, and can display the automatically decided position of each leaf plate 1 and an image of the maximum section of the irradiation field in a superimposed relation. At this time, the doctor can provide an instruction to finely change and adjust the position of each leaf plate 1 with reference to the superimposed images, or the position of each leaf plate 1 can be decided in response to an operation instruction provided by the doctor while the superimposed images are displayed. The decision result of the position of each leaf plate 1 is promptly reflected in the display on the display device.

Based on both the leaf-plate set position information and the irradiation compensator information, the remedy scheduling unit 24 simulates a radiation dose distribution in the patient body and displays a calculation result of the dose distribution on the display device. On that occasion, irradiation parameters such as the radiation dose irradiated to the patient and the radiation energy are given by the doctor, and the simulation is performed for each of the selected several irradiating directions. The doctor finally selects the irradiating direction in which the most preferable result was obtained. The selected irradiating direction and the associated set position information for the leaf plates 1 of the multi-leaf collimator 200, irradiation compensator data, and irradiation parameters are stored in the patient database as remedy data specific to the patient.

(4-2) Control Unit 23 and Collimator Controller 22

The control unit 23 comprises an input device and a display device, which serve as a user operation interface. Also, the control unit 23 is able to acquire the patient remedy data, including the set position information for the leaf plates 1 decided in the remedy scheduling unit 24, via network connection from the patient database associated with the remedy scheduling unit 24, and to display the acquired data on the display device for confirmation by the doctor, etc. Then, in practical irradiation, when a user of the set position information for the leaf plates 1 (a doctor or a radiotherapeutic engineer engaged in assisting the doctor's remedy based on the remedy schedule), for example, inputs the start of irradiation remedy, the control unit 23 outputs a command for starting movement of the leaf plates to the collimator controller 22 in accordance with the set position information for the leaf plates 1.

In response to the command from the control unit 23, the collimator controller 22 outputs necessary control commands to respective subordinating mechanisms, i.e., the leaf position driving actuator 14, the driving force transmitting/cutoff mechanism 15, and the braking force transmitting/cutoff mechanism 16. Upon receiving the movement start command, the collimator controller 22 controls those subordinating mechanisms so that each leaf plate 1 is moved to the predetermined set position.

(4-3) Control of Leaf Plate Movement to Set Position

Figure 8:
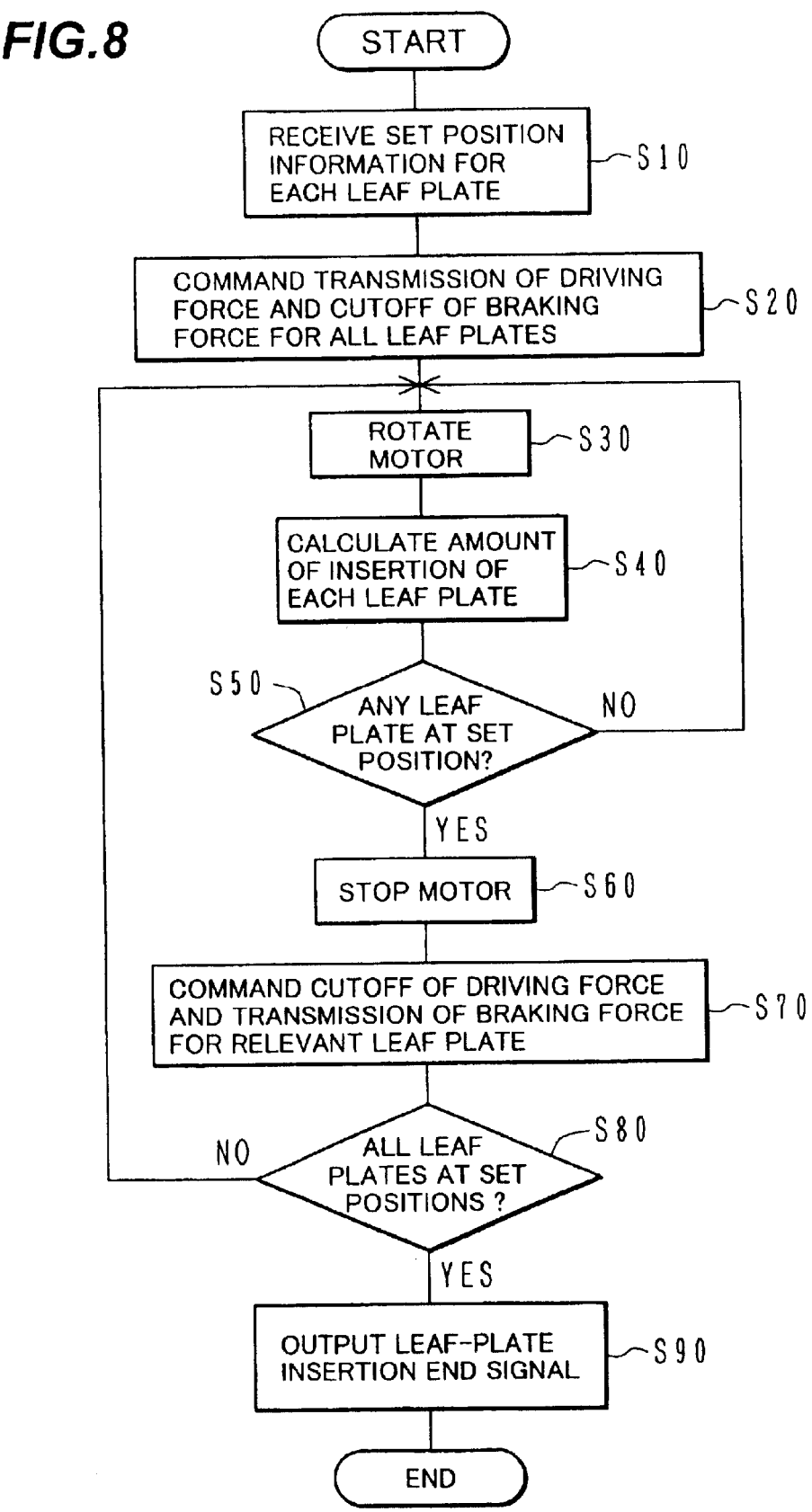
FIG. 8 is a flowchart showing control procedures for moving the leaf plates to set positions by a collimator controller shown in FIG. 2.

The procedures for moving each leaf plate 1 by the collimator controller 22 will first be described with reference to FIG. 8 showing a control flow in this case.

Referring to FIG. 8, the control flow begins when the collimator controller 22 receives the movement start command from the control unit 23. Note that this flow proceeds in parallel for each of the leaf plate driving body 200L, 200R concurrently.

First, in step 10, the collimator controller 22 receives the set position information for each leaf plate 1 from the control unit 23 and stores it in a storage means (not shown).

Then, in step 20, the driving force transmitting command (which serves also as the braking force cutoff command as described above) for transmitting the driving force to all the leaf plates 1 of the leaf plate driver 200L (or 200R) is outputted to the driving force transmitting/-cutoff mechanism 15 (all the upper and lower air cylinders 2, 4 in this embodiment). With this step, in the leaf plate driver 200L, the upper air cylinders 3 and the lower air cylinders 4 associated with all the leaf plates 1 are brought respectively into the inoperative condition and the operative condition (in the leaf plate driver 200R, the upper air cylinders 3 and the lower air cylinders 4 associated with all the leaf plates 1 are brought respectively into the operative condition and the inoperative condition). Thus, all the leaf plates 1 associated with the leaf plate driver 200L (or 200R) are moved away from the braking plate 9 and are meshed with the pinion gear 6.

Next, in step 30, the collimator controller 22 outputs, to the leaf position driving actuator 14 (servo motor 8 in this embodiment), a rotation driving command (leaf advance command) to rotate the motor 8 in the leaf advancing direction (=inserting direction, i.e., direction to narrow the space gap G corresponding to the irradiation field F). Responsively, the motor 8 of the leaf plate driver 200L (or 200R) starts rotation, whereupon all the leaf plates 1 start moving forward in the inserting direction in a transversely aligned state.

Then, in step 40, an amount of insertion (current position) of each leaf plate 1 is detected. Specifically, the collimator controller 22 receives a rotation signal (aforesaid pulse signal) outputted from the servo motor 8 which serves as the position detecting mechanism 19, and determines a rotation angle of the pinion gear 6 from the rotation signal. Further, the collimator controller 22 determines an amount of movement of each leaf plate 1 from both the rotation angle and a gear ratio of a rack-and-pinion mechanism comprising the pinion gear 6 and the rack gear 12, and totalizes the amount of movement from the origin, thereby obtaining current position information for each leaf plate 1.

Subsequently, the control flow proceeds to step 50 where it is determined whether any of all the leaf plates 1 has reached the set position of the relevant leaf plate 1, which is defined by the leaf-plate set position information stored in the collimator controller 22. If not so, the control flow returns to step 20 for repeating the above-described steps in the same manner, and if so, the control flow proceeds to step 60.

In step 60, the collimator controller 22 outputs a driving stop command (leaf stop command) to the leaf position driving actuator 14 (servo motor 8 in this embodiment). In accordance with that command, the rotation of the motor 8 is stopped and the movements of all the leaf plates 1 are stopped simultaneously.

Thereafter, in step 70, the driving force cutoff command (which serves also as the braking force transmitting command as described above) is outputted to the driving force transmitting/cutoff mechanism 15 (upper and lower air cylinders 2, 4) associated with the leaf plate 1 that has reached the set position. With this step, in the leaf plate driver 200L, the lower air cylinder 4 and the upper air cylinder 3 associated with the relevant leaf plate 1 are brought respectively into the inoperative condition and the operative condition (in the leaf plate driver 200R, the lower air cylinder 4 and the upper air cylinder 3 associated with the relevant leaf plate 1 are brought respectively into the operative condition and the inoperative condition). Thus, the relevant leaf plate 1 is out of mesh with (disengaged from) the pinion gear 6, moves away (departs) from it, and is brought into contact with the braking plate 9. As a result, the relevant leaf plate 1 is held stationary at the set position with stability.

Then, in step 80, it is determined whether all the leaf plates 1 associated with the leaf plate driver 200L (or 200R) have reached the set positions. If not so, the control flow returns to step 20 for repeating the above-described steps in the same manner until all the leaf plates 1 reach the set positions. More specifically, in step 20, the rotation of the motor 8 is started again, whereby all of the remaining leaf plates 1 start moving forward again while leaving the leaf plate 1 at the set position, which has reached there in above step 70. Then, through steps 20 to 70, the operations of stopping all the remaining leaf plates 1 upon one leaf plate 1 reaching the set position, cutting off the driving force (making disengagement) and transmitting the braking force for only the relevant one leaf plate 1, transmitting the driving force (making engagement) again and releasing the braking force again for the remaining leaf plates 1, and resuming insertion of the remaining leaf plates 1 are repeated until all the leaf plates 1 are completely moved to the set positions and the driving force is cut off for all the leaf plates 1.

When all the leaf plates 1 have reached the set positions and the driving force is cut off for all the leaf plates 1, the determination in step 80 is satisfied and the collimator controller 22 outputs a leaf-plate insertion end signal to the control unit 23 in step 90, thereby completing the control flow.

In the above-described steps, the current position information and the driving status of each leaf plate 1 under management of the collimator controller 22 are always transmitted to the control unit 23 and displayed on the display device of the control unit 23.

(4-4) Return Control of Leaf Plate to Origin Position

When the leaf plates have all been positioned to the set positions as described above and then irradiation of a radiation beam is ended, the control unit 23 outputs a leaf-plate return-to-origin command to the collimator controller 22 upon the end of irradiation remedy being instructed from the user of the set position information for the leaf plates 1. Upon receiving the return-to-origin command from the control unit 23, the collimator controller 22 controls the aforesaid subordinating mechanisms to move each leaf plate 1 for return to the origin position in a similar but reversed manner to that described above in (4–3).

Figure 9:
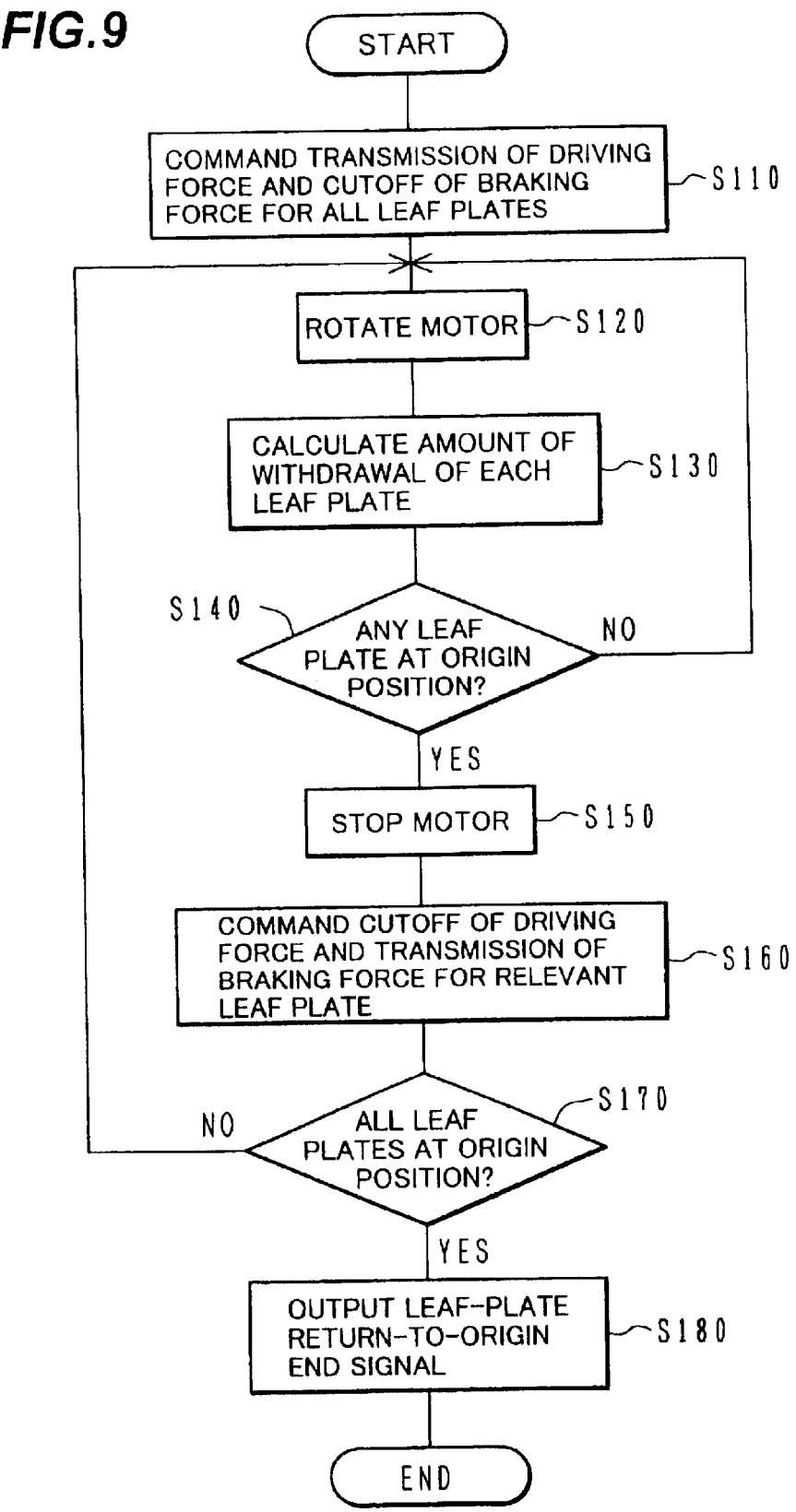
FIG. 9 is a flowchart showing control procedures for returning the leaf plates to the origin positions by the collimator controller shown in FIG. 2.

The procedures for returning each leaf plate 1 to the origin by the collimator controller 22 will be described with reference to FIG. 9 showing a control flow in this case.

Referring to FIG. 9, the control flow begins when the collimator controller 22 receives the return-to-origin command from the control unit 23. Note that, similarly to the flow of FIG. 8, this flow also proceeds in parallel for each of the leaf plate driving body 200L, 200R concurrently.

First, in step 110, the driving force transmitting command (which serves also as the braking force cutoff command) for transmitting the driving force to all the leaf plates 1 of the leaf plate driver 200L (or 200R) is outputted to the driving force transmitting/cutoff mechanism 15 (upper and lower air cylinders 2, 4). With this step, in the leaf plate driver 200L, the upper air cylinders 3 and the lower air cylinders 4 associated with all the leaf plates 1 are brought respectively into the inoperative condition and the operative condition (in the leaf plate driver 200R, the upper air cylinders 3 and the lower air cylinders 4 associated with all the leaf plates 1 are brought respectively into the operative condition and the inoperative condition). Thus, all the leaf plates 1 associated with the leaf plate driver 200L (or 200R) are moved away from the braking plate 9 and are meshed with the pinion gear 6.

Next, in step 120, the collimator controller 22 outputs, to the leaf position driving actuator 14 (servo motor 8 in this embodiment), a rotation driving command (leaf retreat command) to rotate the motor 8 in the leaf retreating direction (=withdrawing direction, i.e., direction to widen the aforesaid space gap G). Responsively, the motor 8 of the leaf plate driver 200L (or 200R) starts rotation, whereupon all the leaf plates 1 start moving backward in the withdrawing direction in a transversely not-aligned state (position difference among the leaf plates 1 remain the same).

Then, in step 130, an amount of withdrawal (current position) of each leaf plate 1 is detected. Specifically, as with the above case, the collimator controller 22 determines an amount of movement of each leaf plate 1 from a rotation signal outputted from the servo motor 8 which serves as the position detecting mechanism 19, and obtains current position information for each leaf plate 1 based on the determined amount of movement. In step 140, it is determined whether any of all the leaf plates 1 has reached the origin position. If not so, the control flow returns to step 120 for repeating the above-described steps in the same manner, and if so, the control flow proceeds to step 150. In step 150, the collimator controller 22 outputs a driving stop command (leaf stop command) to the leaf position driving actuator 14 (motor 8). In accordance with that command, the rotation of the motor 8 is stopped and the movements of all the leaf plates 1 are stopped simultaneously while they remain in the transversely not-aligned state.

Instead of above steps 130 to 150, this embodiment may be modified such that, for example, a limit switch (not shown) is provided beforehand in the vicinity of the origin at a certain distance, and when one leaf plate 1 is withdrawn to a position near the origin and contacts the limit switch, a signal indicating the arrival of the relevant leaf plate 1 to the position near the origin is outputted from the limit switch to the collimator controller 22. In such a modified case, for example, at the timing at which the relevant leaf plate 1 is further withdrawn and an amount of withdrawal of the relevant leaf plate 1 from the time having received the above signal becomes equal to the distance from the limit switch to the origin, the driving stop command is outputted to the motor 8 so as to stop the movements of all the leaf plates 1 simultaneously.

Thereafter, the control flow proceeds to step 160 where the driving force cutoff command (which serves also as the braking force transmitting command) is outputted to the driving force transmitting/cutoff mechanism 15 (upper and lower air cylinders 2, 4) associated with the leaf plate 1 that has reached the origin position. With this step, in the leaf plate driver 200L, the lower air cylinder 4 and the upper air cylinder 3 associated with the relevant leaf plate 1 are brought respectively into the inoperative condition and the operative condition (in the leaf plate driver 200R, the lower air cylinder 4 and the upper air cylinder 3 associated with the relevant leaf plate 1 are brought respectively into the operative condition and the inoperative condition). Thus, the relevant leaf plate 1 is out of mesh with (disengaged from) the pinion gear 6, moved away (departs) from it, and is brought into contact with the braking plate 9. As a result, the relevant leaf plate 1 is completely returned to the origin position and is held stationary there with stability.

Then, in step 170, it is determined whether all the leaf plates 1 associated with the leaf plate driver 200L (or 200R) have returned to the origin positions. If not so, the control flow returns to step 110 for repeating the above-described steps in the same manner until all the leaf plates 1 return to the origin positions. More specifically, in step 110, the rotation of the motor 8 is started again, whereby all of the remaining leaf plates 1 are withdrawn again in the retreating direction while they remain in the transversely not-aligned state. Then, through steps 110 to 170, the operations of stopping all the remaining leaf plates 1 upon one leaf plate 1 returning to the origin position, cutting off the driving force (making disengagement) and transmitting the braking force for only the relevant one leaf plate 1, transmitting the driving force (making engagement) again and releasing the braking force again for the remaining leaf plates 1, and resuming withdrawal of the remaining leaf plates 1 are repeated until all the leaf plates 1 are completely returned to the origin positions and the driving force is cut off for all the leaf plates 1.

When all the leaf plates 1 have returned to the origin positions and the driving force is cut off for all the leaf plates 1, the determination in step 170 is satisfied and the collimator controller 22 outputs a leaf-plate return-to-origin end signal to the control unit 23 in step 180, thereby completing the control flow.

In the above-described steps, the current position information and the driving status of each leaf plate 1 under management of the collimator controller 22 are always transmitted to the control unit 23 and displayed on the display device of the control unit 23.

In the foregoing description, the servo motor 8 in each of the leaf plate driving body 200L, 200R constitutes one driving means defined in claim 1, and the pinion gear 6, all the upper and lower air cylinders 2, 4, and all the upper and lower guides 3, 5 cooperatively constitute driving force transmitting means that is capable of transmitting the driving force to a plurality of leaf plates at the same time and cutting off the driving force selectively for each leaf plate.

Also, the servo motor 8 and the pinion gear 6 in each of the leaf plate driving body 200L, 200R constitutes one driving force generating means defined in claim 2, which is provided to be capable of transmitting the driving force to the plurality of leaf plates at the same time. A pair of upper and lower air cylinders 2, 4 and a pair of upper and lower guides 3, 5, which are provided for each leaf plate 1, cooperatively constitute a plurality of engaging/disengaging means that are provided in a one-to-one relation to the plurality of leaf plates and are each capable of selectively engaging and disengaging a corresponding leaf plate with or from the one driving force generating means. Further, the braking plate 9 constitutes holding means capable of abutting against the leaf plates to hold the leaf plates in predetermined positions.

Moreover, the collimator controller 22 constitutes control means, defined in claim 8, for controlling the one driving means and the driving force transmitting means, and constitutes control means, defined in claim 9, for controlling the one driving force generating means and the engaging/disengaging means.

(5) Advantages of this Embodiment

With the multi-leaf collimator of this embodiment, as described above (particularly in (3) and (4)), in each of the leaf plate driving body 200L and 200R, the driving force of the one common motor 8 can be transmitted to a plurality of leaf plates 1 at the same time, and the driving force can be selectively cut off for each leaf plate 1. When driving each leaf plate 1 from the origin position to the set position, the driving force is transmitted to the plurality of leaf plates 1 at the same time, causing all the leaf plates 1 to start movement simultaneously. Then, when one leaf plate 1 reaches the set position, the driving force applied to the relevant leaf plate 1 is cut off to leave it at the set position. By repeating such a step, all the leaf plates 1 are successively positioned to the set positions. Conversely, when returning all the leaf plates 1 to the origin positions from the set condition, the driving force is transmitted to all the leaf plates 1 in the different set positions at the same time, causing all the leaf plates 1 to start movement simultaneously while they remain in the transversely not-aligned state. Then, when one leaf plate 1 returns to the origin position, the driving force applied to the relevant leaf plate 1 is cut off to hold it at the origin position. By repeating such a step, all the leaf plates 1 are successively returned to the origin positions.

Thus, since the leaf plates 1 can be successively positioned in each of the leaf plate driving body 200L and 200R while moving a plurality of leaf plates at the same time, a time required for completing the formation of the irradiation field, when the irradiation field is to be formed with high accuracy, can be shortened in comparison with a conventional structure wherein a number of leaf plates must be positioned one by one successively in each leaf plate driver. As a result, physical and mental burdens imposed on patients can be reduced.

A second embodiment of the present invention will be described with reference to FIGS. 10 to 12. In this embodiment, the support structure of each leaf plate 1 is modified, and the driving force transmitting/cutoff mechanism 15 and the braking force transmitting/cutoff mechanism 16 are separately provided. The same components as those in the first embodiment are denoted by the same reference numerals, and a description of those components is omitted herein.

Figure 10:
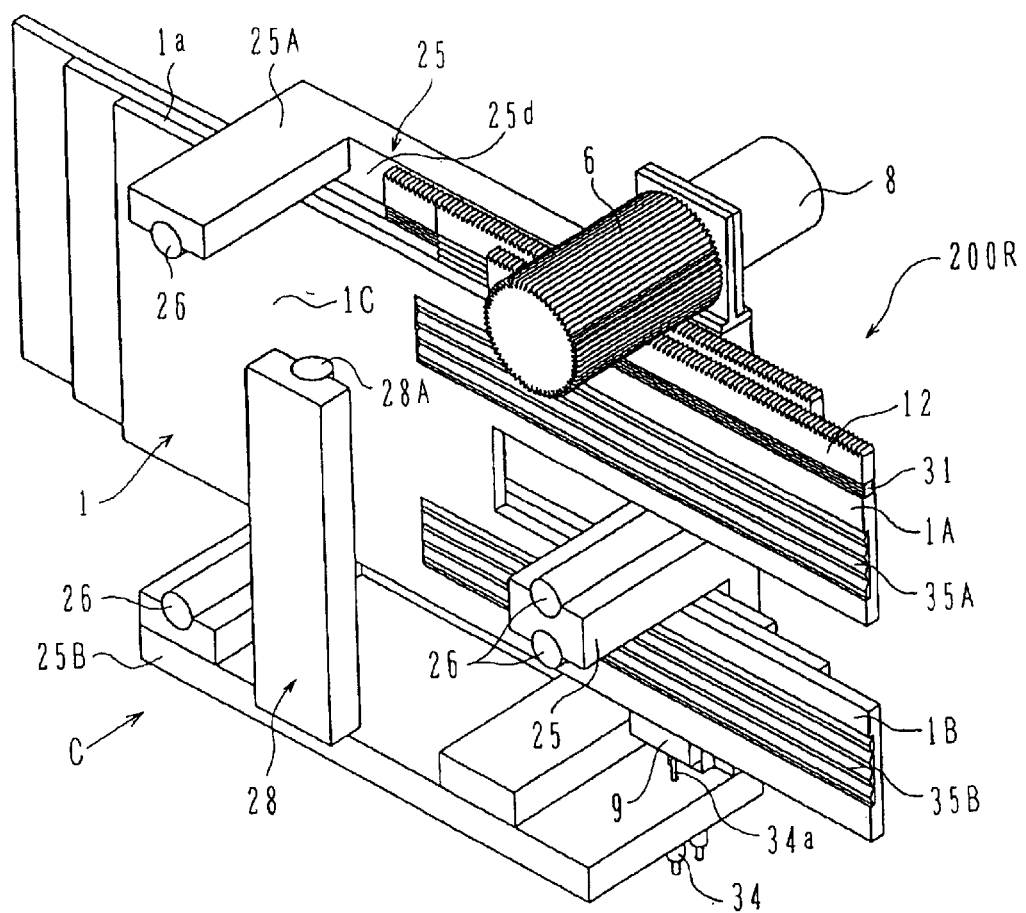
FIG. 10 is a perspective view showing the structure of principal parts of a leaf plate driver provided in a multi-leaf collimator according to a second embodiment of the present invention.

FIG. 10 is a perspective view showing the structure of principal parts of a leaf plate driver 200R provided in a multi-leaf collimator of this embodiment. For the sake of simplicity, only three of total twelve leaf plates 1 are shown in FIG. 10. FIG. 11 is a front view as viewed in the direction of C in FIG. 10, and FIG. 12 is a perspective view showing the detailed structure of one leaf plate 1 in FIGS. 10 and 11.

Figure 11:
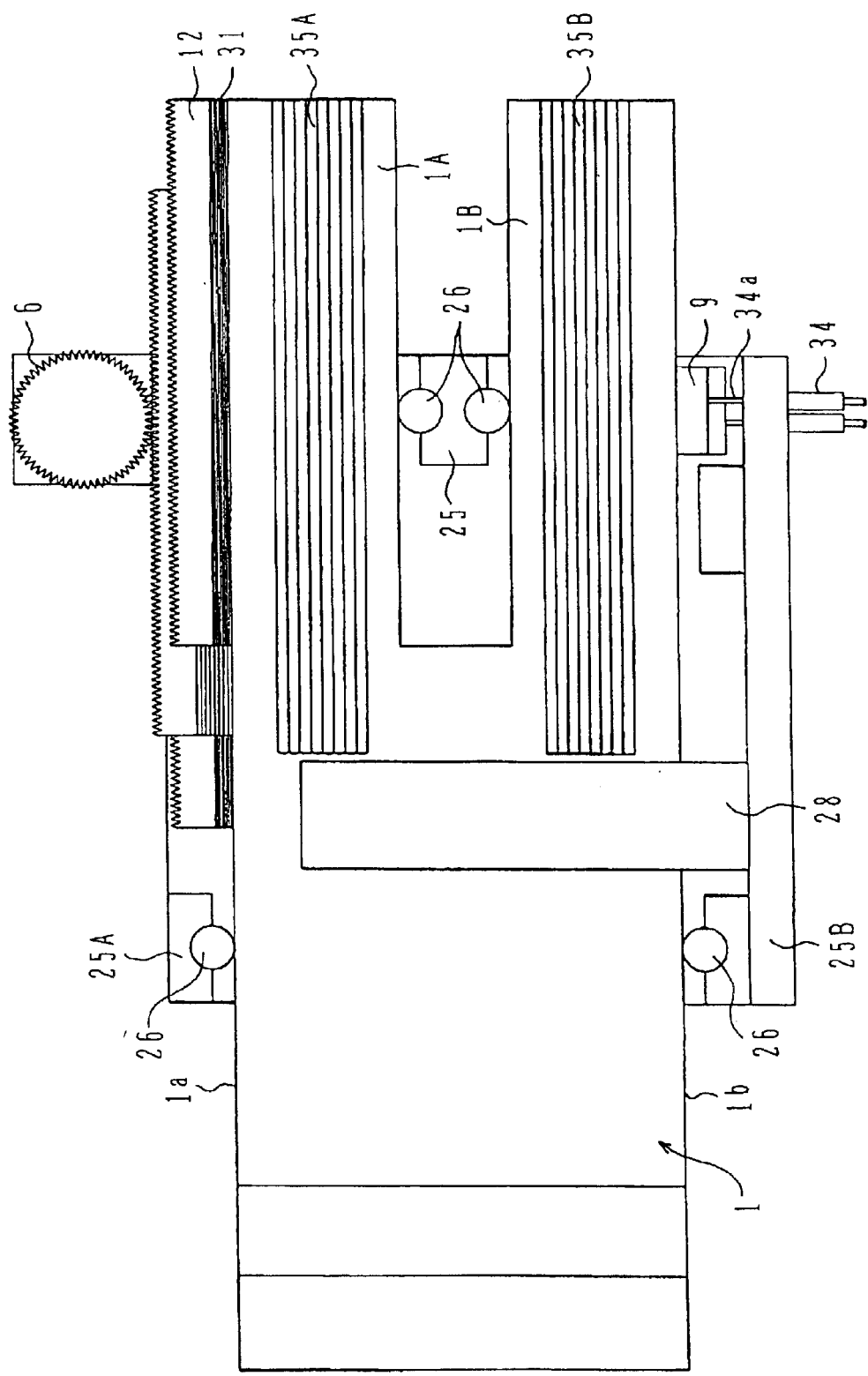
FIG. 11 is a front view of the multi-leaf collimator as viewed in the direction of C in FIG. 10.
Figure 12:
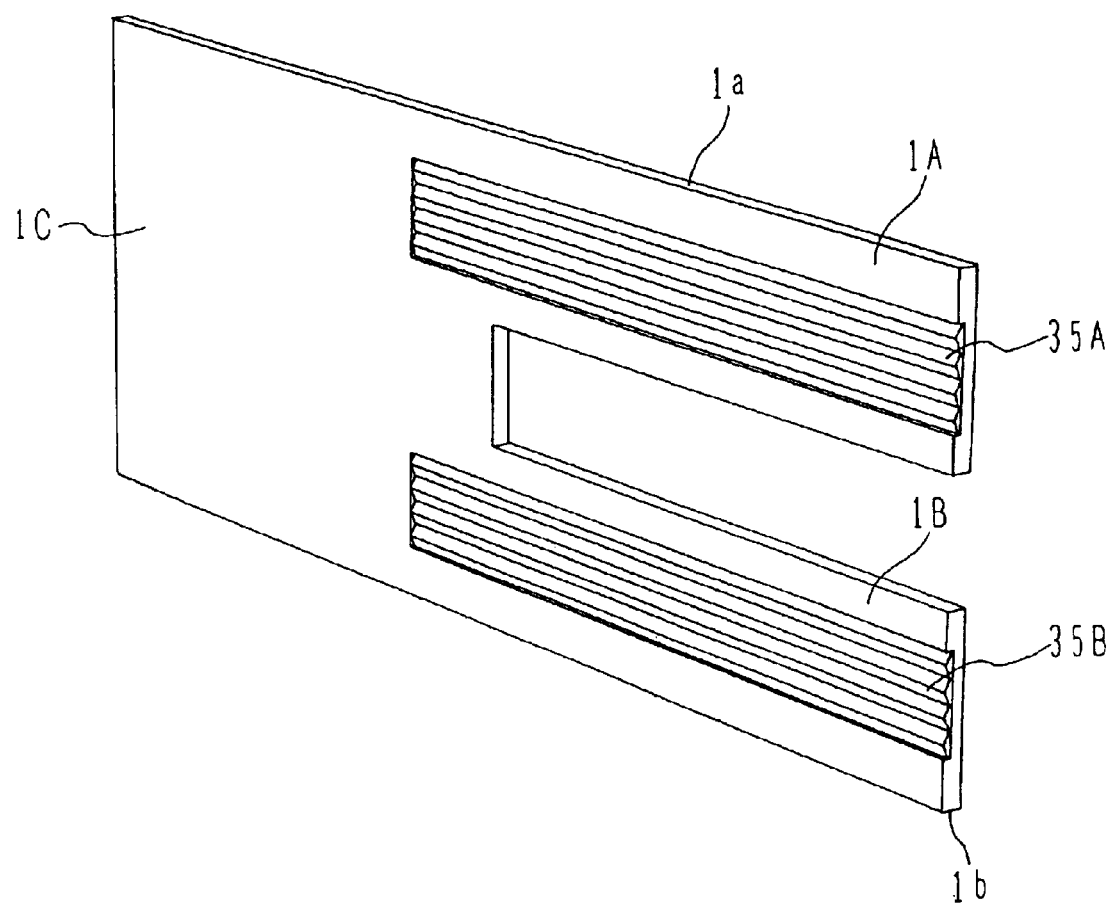
FIG. 12 is a perspective view showing the detailed structure of one leaf plate in FIGS. 10 and 11.

Referring to FIGS. 10, 11 and 12, in the leaf plate driver 200R provided in the multi-leaf collimator of this embodiment, a vertical position of each leaf plate 1 is always held constant. More specifically, an upper end 1a and a lower end 1b of each leaf plate 1 are contacted with respective rollers 26 rotatably provided on an upper projection 25A and a lower bottom plate 25B of a housing 25. Also, a lower edge of an upper sliding portion 1A and an upper edge of a lower sliding portion 1B of each leaf plate 1 are contacted with respective rollers 26 rotatably provided on upper and lower surfaces of an intermediate projection 25C of the housing 25. With such a structure, the leaf plate 1 is able to slide in the longitudinal direction thereof (left and right direction in FIG. 11) while its vertical displacement is restricted by the rollers 26.

On the other hand, a position of each leaf plate 1 in the thickness direction thereof is maintained with such an arrangement that all the leaf plates 1 are sandwiched between a pressing mechanism 28 vertically provided on the housing lower bottom plate 25B and a housing body 25d disposed to extend in the vertical direction. More specifically, the pressing mechanism 28 includes a rotatable roller 28A, which is contacted with one of the total twelve leaf plates 1 positioned closest to the pressing mechanism 28. Though not shown, the housing body 25d also includes a rotatable roller, similar to the roller 28A, which is contacted with one of the twelve leaf plates 1 positioned closest to the housing body 25d. Thus, outermost two of the total twelve leaf plates 1 in the thickness direction thereof are restricted by the rollers from both sides, whereby the total twelve leaf plates 1 are each restricted from displacing in the thickness direction.

On both lateral surfaces of the upper sliding portion 1A and the lower sliding portion 1B of each leaf plate 1, frictional sliding members 35A, 35B are provided in contact with the adjacent leaf plates 1. Since the pressing mechanism 28 applies a load for pressing all the leaf plates 1 toward the housing body 25d, the leaf plates 1 are held in a condition contacting with each other at the frictional sliding members 35A, 35B. The pressing load applied to the leaf plates 1 from the pressing mechanism 28 is adjusted such that the leaf plates 1 are slidable individually.

A rack gear 12 is disposed at the top of the upper sliding portion 1A of each leaf plate through an air-cushion mechanism 31. A pinion gear 6 connected to the motor 8 is provided in an opposing relation to the rack gear 12 of each leaf plate 1. When compressed air is introduced to the air-cushion mechanism 31 through a piping system (not shown) and the air-cushion mechanism 31 is vertically expanded (=in operative condition), the rack gear 12 is raised up into mesh with the pinion gear 6 for transmitting the driving force. When the compressed air is discharged through a piping system (not shown), the air-cushion mechanism 31 is contracted and the rack gear 12 is out of mesh with the pinion gear 6, thereby disabling (cutting off) the transmission of the driving force. Stated otherwise, the air-cushion mechanism 31 provided for each leaf plate 1 fulfills the function of the driving force transmitting/-cutoff mechanism 15 described above in the first embodiment with reference to FIG. 7.

Further, in this embodiment, an air cylinder 34 for moving a braking plate 9 up and down serves as the braking force transmitting/cutoff mechanism 16 shown in FIG. 7. More specifically, the air cylinder 34 is provided on the backside (underside) of the housing bottom plate 25B in a one-to-one relation to the leaf plates 1, and has a rod 34a penetrating the housing bottom plate 25B to project upward. The braking plate 9 is connected to a fore end of the rod 34a. As with the air cylinders 2, 4 used in the first embodiment of the present invention, the air cylinder 34 is constituted by a known single- or double-actuated air cylinder. When compressed air is supplied from a compressed air source to a bottom-side chamber, the rod 34a is extended (operative condition), the braking plate 9 is raised upward to such an extent that an upper surface of the braking plate 9 abuts against the leaf plate lower end 1b to produce braking force. The leaf plate 1 is hence stopped and held at that position by frictional force.

Subsequently, when the compressed air supplied to the bottom-side chamber is discharged (for example, by being made open to the atmosphere), a piston is returned to the bottom side by the biasing force of a spring. As a result, the rod 34a is contracted (inoperative or stop condition) for return to the original position so that the leaf plate is made free (released) from the braking force. Thus, in this embodiment, the air cylinder 34 provided for each leaf plate 1 serves as the braking force transmitting/cutoff mechanism 16 described above in connection with FIG. 7. Additionally, the braking plate 9 comes into contact with the leaf plate 1 and generates frictional braking force only when the air cylinder 34 is operated to raise the braking plate 9 upward.

While the above description is made in connection with, for example, the leaf plate driver 200R on one side, the leaf plate driver 200L on the other side is of the same structure.

Control procedures for driving the leaf plates 1 in this embodiment having the above-mentioned construction are basically the same as those in the first embodiment described above with reference to FIGS. 8 and 9 except that the transmission/cutoff of the driving force and the transmission/cutoff of the braking force are separately controlled. More specifically, the procedures for moving the leaf plates 1 to the set positions, described above in connection with FIG. 8, and the procedures for returning the leaf plates 1 to the origin positions, described above in connection with FIG. 9, are modified as follows. In steps 20 and 110, a driving force transmitting command for transmitting the driving force to the leaf plates 1 is outputted to the air-cushion mechanism 31 that serves as the driving force transmitting/cutoff mechanism 15, and a braking force cutoff command is outputted to the air cylinder 34 that serves as the braking force transmitting/Attorney cutoff mechanism 16. In accordance with those commands, the air-cushion mechanism 31 is brought into the operative condition and the air cylinder 34 is brought into the inoperative condition, respectively, whereby the braking plate 9 departs away from the leaf plate 1 and the pinion gear 6 meshes with the rack gear 12. Also, in steps 70 and 160, a driving force cutoff command for cutting off the driving force applied to the leaf plates 1 is outputted to the air-cushion mechanism 31, and a braking force transmitting command is outputted to the air cylinder 34. In accordance with those commands, the air-cushion mechanism 31 is brought into the inoperative condition and the air cylinder 34 is brought into the operative condition, respectively, whereby the braking plate 9 contacts with the leaf plate 1 and the pinion gear 6 is out of mesh with the rack gear 12.

In the foregoing description, the pinion gear 6 and all the air-cushion mechanisms 31 in each of the leaf plate driving body 200L, 200R cooperatively constitute driving force transmitting means defined in claim 1, which is capable of transmitting the driving force to a plurality of leaf plates at the same time and cutting off the driving force selectively for each leaf plate.

Also, the air-cushion mechanisms 31 provided in each of the leaf plate driving body 200L, 200R in a one-to-one relation to the leaf plates 1 constitute a plurality of engaging/-disengaging means that are provided in a one-to-one relation to the plurality of leaf plates and are each capable of selectively engaging and disengaging a corresponding leaf plate with or from the one driving force generating means.

This embodiment can also provide similar advantages as those in the first embodiment of the present invention.

While the driving force is transmitted in the first and second embodiments through meshing of the pinion gear 6 with the rack gear 12, the present invention is not limited to such an arrangement. For example, the arrangement may be modified such that a rubber roller having a cylindrical shape is provided instead of the pinion gear 6, the upper and lower edges of the upper and lower sliding portions 1A, 1B of each leaf plate 1 are each formed in an ordinary shape without the rack gear 12, and the rubber roller is brought into engagement with the upper and lower edges of the upper and lower sliding portions 1A, 1B for transmitting the driving force through frictional force produced upon the engagement. This modification can also provide similar advantages.

Further, in the first and second embodiments, the upper and lower air cylinders 2, 4 or the air cylinders 34 are used as the driving force transmitting/cutoff mechanism 15 or the braking force transmitting/cutoff mechanism 16. Instead of those cylinders, however, known linearly reciprocating actuators provided with solenoid magnets (electromagnets) may be used. This modification can also provide similar advantages.

While the first and second embodiments employ the servo motor 8 as the leaf position driving actuator 14, a stepping motor may be used instead. A stepping motor is a motor that rotates through a minute angle for each pulse when a pulse-shaped signal is applied as a drive signal to the motor. Usually, a rotation angle per pulse of the drive signal is reliably provided with high accuracy. In this modification, the drive signal for driving the stepping motor can be used instead of the rotation signal obtained from the servo motor 8 in the first and second embodiments. This modification can also provide similar advantages.

In the first and second embodiments, the servo motor 8 functions also as the position detecting mechanism 19. However, the present invention is not limited to such an arrangement, and the position detecting mechanism 19 may be constituted by a linear encoder separately provided. A linear encoder comprises, for example, a rotary encoder, a wire, and a winding reel. The reel is rotated corresponding to the distance through which the wire is drawn out, and the rotary encoder connected to the reel generates a rotation signal. In this modification, the linear encoder is provided in the same number as the leaf plates 1 because it is connected to each leaf plate 1 in a one-to-one relation. Then, each linear encoder always outputs, to the collimator controller 22, pulse signals corresponding to the distance of movement of the leaf plate 1 connected to that linear encoder. Based on the known relationship between the pulse signal and the distance of movement of the leaf plate, the collimator controller 22 adds up the distance of movement of each leaf plate 1 and stores it therein as the position information.

Furthermore, instead of the linear encoder, another type of linear displacement detector may be connected to each leaf plate 1. Other types of linear displacement detector include, for example, a linear scale, a linear potentiometer, and an LVDT (Linear Variable Differential Transformer).

A linear scale comprises a linear rule and a reading head. The reading head moving over the linear rule optically or magnetically reads position symbols disposed on the rule with minute intervals, and outputs a pulse signal. A position detecting method based on a pulse signal is the same as the case described above.

A linear potentiometer comprises a linear resistor and a slider linearly moving in slide contact with the resistor. Based on the fact that a resistance value between a terminal connected to one end the resistor and a terminal connected to the slider is given by a resistance value corresponding to the length of the resistor from the resistor terminal to the slider position, the resistance value is linearly changed depending on the distance through which the slider has moved. By connecting a power supply between both the terminals and measuring a voltage therebetween, the resistance value is read after transformation into voltage. In this case, the collimator controller 22 reads the voltage through an A/D converter and calculates the amount of movement of the slider (leaf plate) based on both the relationship between resistance value and voltage in a resistance—voltage converter and the linear relationship between displacement and resistance value, which is specific to the linear potentiometer.

An LVDT comprises a unit made up of an excited primary coil and a secondary coil which are coaxially arranged side by side, and an iron core arranged to lie at the centers of the primary coil and the secondary coil and to extend in a straddling relation to both the coils. A linear displacement of the iron core connected to a measurement target is outputted as a change in an output voltage of the secondary coil, which is produced as the strength of coupling between the primary coil and the secondary coil changes. Design parameters are set such that the relationship between displacement and output voltage is linear and provides a constant gradient. Manners for reading the voltage and calculating the displacement are similar to those in the above case.

According to the present invention, as described above, it is possible to shorten a positioning time required for forming an irradiation area with high accuracy using a number of leaf plates, and to reduce physical and mental burdens imposed on patients.

What is claimed is:

1. A multi-leaf collimator comprising a first leaf plate driving body provided on a first side of the collimator and a second leaf plate driving body provided on a second side of the collimator, the first and second leaf plate driving bodies each including a plurality of movable leaf plates, the plurality of leaf plates of said leaf plate driving body on the first side and the plurality of leaf plates of said leaf plate driving body on the second side being disposed in an opposing relation to form an irradiation field of a radiation beam between the opposing leaf plates, wherein:

each of said first and second leaf plate driving bodies comprises one rotating device for moving said plurality of leaf plates along one direction by engaging with a gear portion provided respectively at each of said plurality of leaf plates, and a driving force transmitting/cutoff device for transmitting a driving force of said rotating device to said plurality of leaf plates at the same time during a certain period by moving said plurality of gear portions along a direction substantially perpendicular to said one direction and engaging them with said rotating device and cutting off said driving force to a selected one of said plurality of leaf plates by disengaging said gear portion of said selected leaf plate from said rotating device.

2. A multi-leaf collimator according to claim 1, wherein each of said first and second leaf plate driving bodies further comprises a holding device for abutting against the leaf plates to hold the leaf plates in stationary positions.

3. A multi-leaf collimator comprising a first leaf plate driving body provided on a first side of the collimator and a second leaf plate driving body provided on a second side of the collimator, the first and second leaf plate driving bodies each including a plurality of movable leaf plates, the plurality of leaf plates of said leaf plate driving body on the first side and the plurality of leaf plates of said leaf plate driving body on the second side being disposed in an opposing relation to form an irradiation field of a radiation beam between the opposing leaf plates, wherein:

each of said first and second leaf plate driving bodies comprises one rotating device for moving said plurality of leaf plates together along one direction during a certain period by engaging with a gear portion provided respectively at each of said plurality of leaf plates, and a plurality of engaging/disengaging devices provided in a one-to-one relation to the plurality of leaf plates for selectively engaging and disengaging a corresponding leaf plate with and from said rotating device by moving said gear portion of said corresponding leaf plate along a direction substantially perpendicular to said one direction.

4. A multi-leaf collimator according to claim 3, wherein each of said first and second leaf plate driving bodies further comprises a holding device for abutting against the leaf plates to hold the leaf plates in stationary positions.

5. A medical system comprising:

an accelerator; and an irradiator having a collimator through which a radiation beam emitted from said accelerator passes, and irradiating the beam having passed said collimator, wherein:

said collimator comprises a first leaf plate driving body provided on a first side of the collimator and a second leaf plate driving body provided on a second side of the collimator, the first and second leaf plate driving bodies each including a plurality of movable leaf plates, the plurality of leaf plates of said first and second leaf plate driving bodies being disposed in an opposing relation to form an irradiation field of the radiation beam between the opposing leaf plates, each of said first and second leaf plate driving bodies comprises one rotating device for moving said plurality of leaf plates along one direction by engaging with a gear portion provided respectively at each of said plurality of leaf plates, and a driving force transmitting/cutoff device for transmitting a driving force of said rotating device to said plurality of leaf plates at the same time during a certain period by moving said plurality of gear portions along a direction substantially perpendicular to said one direction and engaging them with said rotating device and cutting off said driving force to a selected one of said plurality of leaf plates by disengaging said gear portion of said selected leaf plate from said rotating device.

6. A medical system according to claim 5, further comprising a control device for controlling said rotating device and said transmitting/cutoff device.

7. A medical system comprising:

an accelerator; and an irradiator having a collimator through which a radiation beam emitted from said accelerator passes, and irradiating the beam having passed said collimator, wherein:

said collimator comprises a first leaf plate driving body provided on a first side of the collimator and a second leaf plate driving body provided on a second side of the collimator, the first and second leaf plate driving bodies each including a plurality of movable leaf plates, the plurality of leaf plates of said first and second leaf plate driving bodies being disposed in an opposing relation to form an irradiation field of the radiation beam between the opposing leaf plates, each of said first and second leaf plate driving bodies comprises one rotating device for moving said plurality of leaf plates together along one direction during a certain period by engaging with a gear portion provided respectively at each of said plurality of leaf plates, and a plurality of engaging/disengaging devices provided in a one-to-one relation to the plurality of leaf plates for selectively engaging and disengaging a corresponding leaf plate with and from said rotating device by moving said gear portion of said corresponding leaf plate along a direction substantially perpendicular to said one direction.

8. A medical system according to claim 7, further comprising a control device for controlling said rotating device and said engaging/disengaging device.

9. A multi-leaf collimator comprising a first leaf plate driving body provided on a first side of the collimator and a second leaf plate driving body provided on a second side of the collimator, the first and second leaf plate driving bodies each including a plurality of movable leaf plates, the plurality of leaf plates of said leaf plate driving body on the first side and the plurality of leaf plates of said leaf plate driving body on the second side being disposed in an opposing relation to form an irradiation field of a radiation beam between the opposing leaf plates, wherein:

each of said first and second leaf plate driving bodies comprises one rotating device for moving said plurality of leaf plates together along one direction during a certain period by engaging with a gear portion provided respectively at each of said plurality of leaf plates, a plurality of guide members provided in a one-to-one relation to the plurality of leaf plates for holding said leaf plate slidably along said one direction, and a guide member moving device for moving said guide member along a direction substantially perpendicular to said one direction for engaging and disengaging said gear portion with and from said rotating device.

10. A multi-leaf collimator according to claim 9, wherein each of said first and second leaf plate driving bodies further comprise a holding device for abutting against the leaf plates to hold the leaf plates in stationary positions.

11. A multi-leaf collimator comprising a first leaf plate driving body provided on a first side of the collimator and a second leaf plate driving body provided on a second side of the collimator, the first and second leaf plate driving bodies each including a plurality of movable leaf plates, the plurality of leaf plates of said leaf plate driving body on the first side and the plurality of leaf plates of said leaf plate driving body on the second side being disposed in an opposing relation to form an irradiation field of a radiation beam between the opposing leaf plates, wherein:

each of said first and second leaf plate driving bodies comprises one rotating device for moving said plurality of leaf plates together along one direction during a certain period by engaging with a gear portion provided respectively at each of said plurality of leaf plates, each of said plurality of leaf plates provided at each of said first and second plate driving bodies comprises an expansion/contraction member for expanding and contracting along a direction substantially perpendicular to said one direction for engaging and disengaging said gear portion with and from said rotating device, and said gear portion is disposed at said expansion/contraction member.

12. A multi-leaf collimator according to claim 11, wherein each of said first and second leaf plate driving bodies further comprises a holding device for abutting against the leaf plates to hold the leaf plates in stationary positions.

13. A medical system comprising:

an accelerator; and an irradiator having a collimator through which a radiation beam emitted from said accelerator passes, and irradiating the beam having passed said collimator, wherein:

said collimator comprises a first leaf plate driving body provided on a first side of the collimator and a second leaf plate driving body provided on a second side of the collimator, the first and second leaf plate driving bodies each including a plurality of movable leaf plates, the plurality of leaf plates of said first and second leaf plate driving bodies being disposed in an opposing relation to form an irradiation field of the radiation beam between the opposing leaf plates, each of said first and second leaf plate driving bodies comprises one rotating device for moving said plurality of leaf plates together along one direction during a certain period by engaging with a gear portion provided respectively at each of said plurality of leaf plates, a plurality of guide members provided in a one-to-one relation to the plurality of leaf plates for holding said leaf plate slidably along said one direction, and a guide member moving device for moving said guide member along a direction substantially perpendicular to said one direction for engaging and disengaging said gear portion with and from said rotating device.

14. A medical system according to claim 13, further comprising a control device for controlling said rotating device and said guide member moving device.

15. A medical system comprising:

an accelerator; and an irradiator having a collimator through which a radiation beam emitted from said accelerator passes, and irradiating the beam having passed said collimator, wherein:

said collimator comprises a first leaf plate driving body provided on a first side of the collimator and a second leaf plate driving body provided on a second side of the collimator, the first and second leaf plate driving bodies each including a plurality of movable leaf plates, the plurality of leaf plates of said first and second leaf plate driving bodies being disposed in an opposing relation to form an irradiation field of the radiation beam between the opposing leaf plates, each of said first and second leaf plate driving bodies comprises one rotating device for moving said plurality of leaf plates together along one direction during a certain period by engaging with a gear portion provided respectively at each of said plurality of leaf plates, each of said plurality of leaf plates provided at each of said leaf plate driving bodies comprises an expansion/contraction member for expanding and contracting along a direction substantially perpendicular to said one direction for engaging and disengaging said gear portion with and from said rotating device, and said gear portion is disposed at said expansion/contraction member.

* * * * *